US012490993B2

(12) United States Patent
Firmbach et al.

(10) Patent No.: US 12,490,993 B2
(45) Date of Patent: Dec. 9, 2025

(54) ALIGNMENT DEVICE FOR A TIBIAL RESECTION GUIDE

(71) Applicant: Aesculap AG, Tuttlingen (DE)

(72) Inventors: Franz-Peter Firmbach, Emmingen-Liptingen (DE); Roland Boettiger, Rietheim-Weilheim (DE); Berna Richter, Muehlheim (DE)

(73) Assignee: Aesculap AG, Tuttlingen (DE)

(*) Notice: Subject to any disclaimer, the term of this patent is extended or adjusted under 35 U.S.C. 154(b) by 572 days.

(21) Appl. No.: 17/918,993

(22) PCT Filed: Apr. 14, 2021

(86) PCT No.: PCT/EP2021/059647
§ 371 (c)(1),
(2) Date: Oct. 14, 2022

(87) PCT Pub. No.: WO2021/209496
PCT Pub. Date: Oct. 21, 2021

(65) Prior Publication Data

US 2023/0063563 A1 Mar. 2, 2023

(30) Foreign Application Priority Data

Apr. 15, 2020 (DE) ..................... 10 2020 110 346.8

(51) Int. Cl.
*A61B 17/15* (2006.01)
*A61B 17/00* (2006.01)

(52) U.S. Cl.
CPC .... *A61B 17/157* (2013.01); *A61B 2017/0042* (2013.01)

(58) Field of Classification Search
CPC ...................... A61B 17/157; A61B 2017/0042
See application file for complete search history.

(56) References Cited

U.S. PATENT DOCUMENTS 4,621,628 A 11/1986 Brudermann
5,002,547 A 3/1991 Poggie et al.
(Continued)

FOREIGN PATENT DOCUMENTS

CN 205379351 U 7/2016
DE 20105643 U1 6/2001
(Continued)

OTHER PUBLICATIONS

Office Action received in U.S. Appl. No. 17/296,830 dated Jan. 20, 2023, 31 pages.
(Continued)

*Primary Examiner* — Sameh R Boles
(74) *Attorney, Agent, or Firm* — Christopher A. Rothe; CM Law

(57) ABSTRACT

An alignment device for a tibial resection guide includes a clamping device having at least two clamping elements acting against one another for clamping the distal end of a tibia of a patient. A contact device for contacting the proximal end of the tibia includes a tool guiding device for guiding a tool during the resection of the tibia. A telescopic device is separably connected to the contact device and adjustably connected to the clamping device. The telescopic device is designed to align the contact device and clamping device with respect to the tibia. The telescopic device has a decoupling device configured to separate the contact device from the telescopic device when activated. The clamping elements are designed such that the telescopic device can be removed from the tibia with one hand after the decoupling device is activated.

3 Claims, 18 Drawing Sheets

(56) References Cited

U.S. PATENT DOCUMENTS

| | | | | |
|---|---|---|---|---|
| 5,049,151 | A | 9/1991 | Durham et al. | |
| 5,197,944 | A * | 3/1993 | Steele | A61B 17/157 606/86 R |
| 5,514,145 | A | 5/1996 | Durham et al. | |
| 5,628,750 | A | 5/1997 | Whitlock et al. | |
| 5,667,511 | A | 9/1997 | Vendrely et al. | |
| 5,704,941 | A | 1/1998 | Jacober et al. | |
| 6,162,228 | A | 12/2000 | Durham | |
| 6,221,035 | B1 | 4/2001 | Kana et al. | |
| 6,267,762 | B1 | 7/2001 | Millard et al. | |
| 6,277,123 | B1 | 8/2001 | Maroney et al. | |
| 7,344,542 | B2 | 3/2008 | Collazo et al. | |
| 7,785,330 | B2 | 8/2010 | Sherman et al. | |
| 8,998,913 | B2 | 4/2015 | Choong et al. | |
| 9,429,165 | B2 | 8/2016 | Tamaoka et al. | |
| 10,792,049 | B2 | 10/2020 | Fiedler et al. | |
| 2005/0070910 | A1 | 3/2005 | Keene | |
| 2005/0182415 | A1 | 8/2005 | Steffensmeier et al. | |
| 2006/0189998 | A1 | 8/2006 | Rasmussen | |
| 2006/0241639 | A1 | 10/2006 | Kuczynski et al. | |
| 2008/0027471 | A1 | 1/2008 | Hauri | |
| 2010/0087831 | A1 | 4/2010 | Marx | |
| 2012/0053594 | A1 | 3/2012 | Pelletier et al. | |
| 2012/0101504 | A1 | 4/2012 | Habegger et al. | |
| 2014/0324054 | A1 | 10/2014 | Dmuschewsky et al. | |
| 2016/0367291 | A1 | 12/2016 | Erickson et al. | |
| 2017/0245893 | A1 | 8/2017 | Sanders et al. | |
| 2022/0008086 | A1 | 1/2022 | Hirt et al. | |
| 2022/0022889 | A1 | 1/2022 | Hirt et al. | |
| 2022/0160370 | A1 | 5/2022 | Boettinger et al. | |

FOREIGN PATENT DOCUMENTS

| | | | |
|---|---|---|---|
| DE | 69719663 | | 11/2003 |
| DE | 69531388 | | 6/2004 |
| DE | 69630776 | | 9/2004 |
| DE | 60028278 | | 5/2007 |
| DE | 60212852 | | 8/2007 |
| DE | 102006035602 | A1 | 2/2008 |
| DE | 202015101629 | U1 | 7/2015 |
| DE | 102018130117 | A1 | 5/2020 |
| DE | 102019103880 | A1 | 8/2020 |
| EP | 0839501 | A2 | 5/1998 |
| GB | 2398010 | A | 8/2004 |
| JP | 2000300572 | A | 10/2000 |
| JP | 2008125706 | A | 6/2008 |
| JP | 2011092405 | A | 5/2011 |
| JP | 2013071013 | A | 4/2013 |
| JP | 2014195196 | A | 10/2014 |
| JP | 6221035 | B2 | 10/2017 |
| WO | 0071035 | A1 | 11/2000 |
| WO | 03013371 | A1 | 2/2003 |
| WO | 2005110249 | A1 | 11/2005 |
| WO | 2009037479 | A1 | 3/2009 |
| WO | 2012027816 | A1 | 3/2012 |
| WO | 2013134595 | A1 | 9/2013 |
| WO | 2019046518 | A2 | 3/2019 |
| WO | 2020013584 | A1 | 1/2020 |
| WO | 2021209496 | A3 | 10/2021 |

OTHER PUBLICATIONS

Office Action received in Japanese Application No. 2022-562883 dated Nov. 25, 2024, with translation, 6 pages.
International Search Report received in International Application No. PCT/EP2019/082960 dated Feb. 5, 2020, with translation, 5 pages.
International Search Report received in International Application No. PCT/EP2019/082964 dated Mar. 6, 2020, with translation, 10 pages.
Non-final Office Action received in U.S. Appl. No. 17/296,676, dated Mar. 28, 2022.
Office Action received in Japanese Application No. 2021-546788 dated Feb. 25, 2022, with translation, 10 pages.
Search Report received in German Application No. 10 2018 130 117.0 dated Sep. 5, 2019, with translation, 14 pages.
Search Report received in German Application No. 10 2018 130 119.7 dated Sep. 5, 2019, with translation, 11 pages.
Search Report received in German Application No. 10 2019 103 880.4 dated Oct. 23, 2019, with translation, 16 pages.
Search Report received in German Application No. 10 2020 110 346.8 dated Dec. 11, 2020, with translation, 12 bages.
Search Report received in International Application No. PCT/EP2020/053740 dated Oct. 9, 2020, with translation, 5 pages.
Search Report received in International Application No. PCT/EP2021/059647 dated Oct. 12, 2021, with translation, 10 pages.
Written Opinion received in International Application No. PCT/EP2019/082960 dated Feb. 5, 2020, with translation, 13 pages.
Written Opinion received in International Application No. PCT/EP2019/082964 dated Mar. 6, 2020, with translation, 9 pages.
Written Opinion received in International Application No. PCT/EP2020/053740 dated Oct. 9, 2020, with translation, 9 pages.
Written Opinion received in International Application No. PCT/EP2021/059647 dated Oct. 12, 2021, with translation, 29 pages.

* cited by examiner

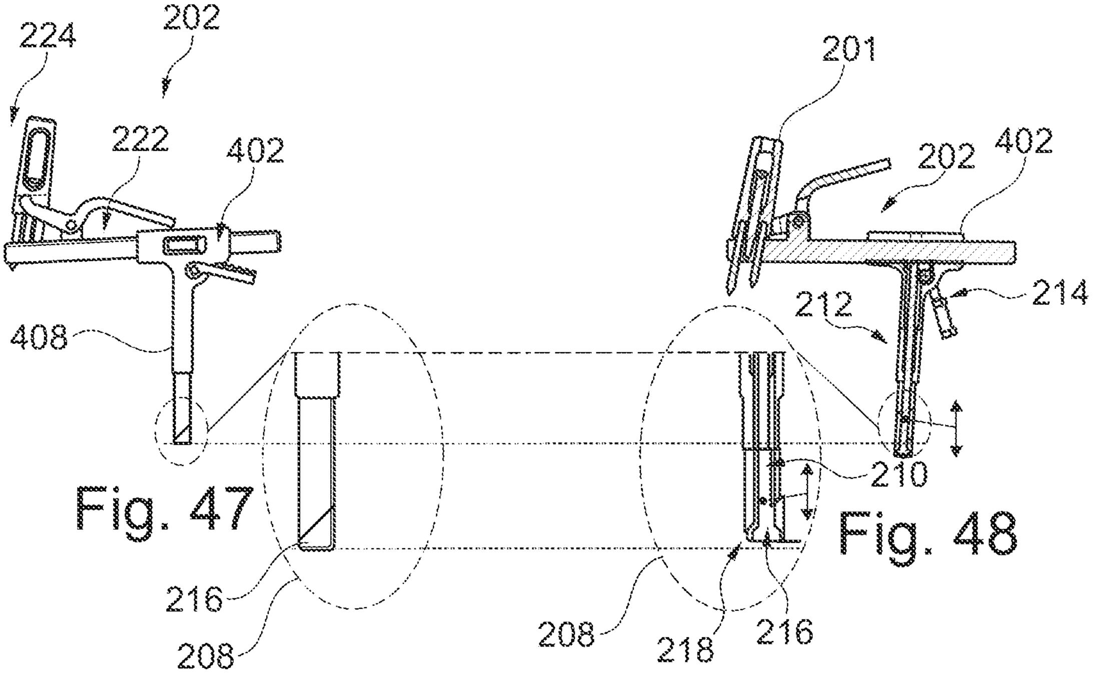
Fig. 47
Fig. 48
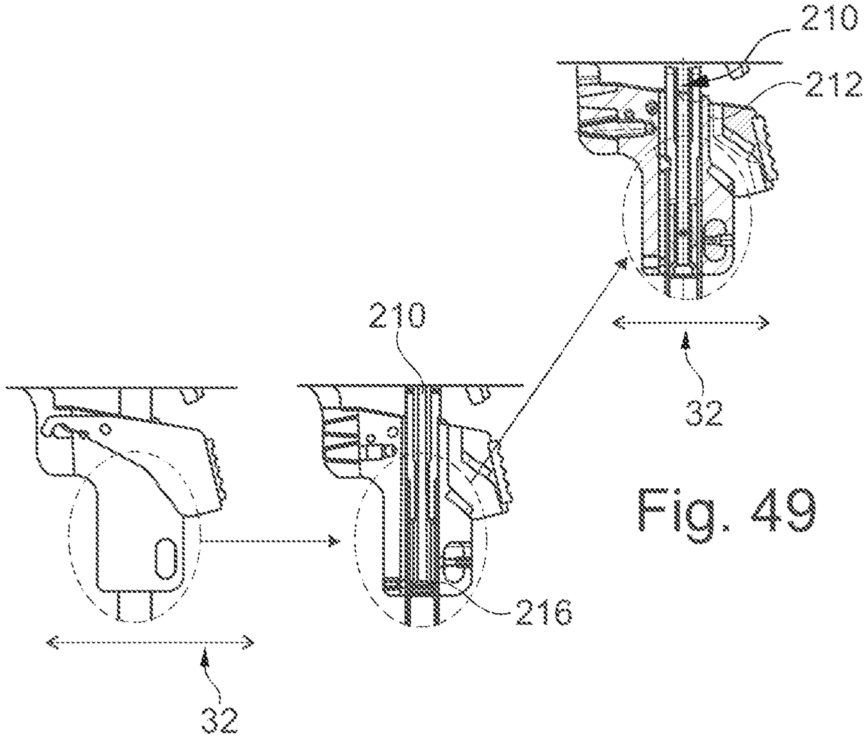
Fig. 49
Fig. 50
Fig. 51

ALIGNMENT DEVICE FOR A TIBIAL RESECTION GUIDE

CROSS-REFERENCE TO RELATED APPLICATIONS

This application is the United States national stage entry of International Application No. PCT/EP2021/059647, filed Apr. 14, 2021, and claims priority to German Application No. 10 2020 110 346.8, filed Apr. 15, 2020. The contents of International Application No. PCT/EP2021/059647 and German Application No. 10 2020 110 346.8 are incorporated by reference herein in their entireties.

FIELD

The present disclosure relates to an alignment device or alignment aid for a tibial resection guide comprising a clamping device which has at least two clamping elements acting against one another for clamping the distal end of a tibia of a patient; which comprises a contact device for contacting the proximal end of the tibia, which device comprises a tool guiding device for guiding a tool during the resection of the tibia; and a telescopic device which is separably connected to the contact device and adjustably connected to the clamping device and is designed to align the devices with respect to the tibia.

BACKGROUND

The precise resection of a patient's bone, especially the tibia, is of great importance for the success of an operation to implant a joint prosthesis. The plane of the resection must be precisely localized in order to minimize a degree of bone removal on the one hand, while at the same time it has to be ensured that all of the defective bone tissue is removed as well. The alignment of the plane in relation to an anatomical axis, in particular a tibial axis, must be continuously monitored during surgery to ensure the alignment of the joint surfaces of the joint over the entire region of joint motion.

The exact definition of a tibial resection plane in a knee joint is usually set using an alignment device or adjustment guide (for a saw block) with a columnar adjustment rod or telescopic device attached remote from the tibia near the ankle. The telescopic device extends along the tibia (essentially) parallel to the corresponding anatomical tibial axis. The resection plane can then be defined in relation to the tibial axis. Finally, a tool guiding device attached to the alignment device defines the plane of resection. Usually, the tool guiding device has a passage slot for this purpose, through which a planar cutting edge, pivoting back and forth, of a surgical instrument (saw) is passed.

In order to adjust the alignment of the tibia resection plane, an alignment device is attached to the tibia, which is connected to the telescopic device at its one end pointing towards a foot of the patient, and the tool guiding device is connected to its other end (end portion). Here, a basic distinction is made between two alignment and fixation principles, namely "anterior fixation" and "proximal fixation". In the case of "anterior fixation", the alignment device is fastened exclusively by means of the foot/ankle shackle described above, whereas in the case of "proximal fixation", additional drive pins are provided at the proximal end portion of the alignment device, which are driven in at the so-called Eminentia intercondylaris tibiae.

U.S. Pat. No. 6,221,035 B1 discloses an ankle/bone shackle in the form of a fixation clamp of an alignment aid of the anterior fixation type used in tibial resection. In this case, the fixation clamp is located at the distal end portion of a telescopic alignment rod, to the distal end portion of which a tibia cut block is mounted.

The clamp itself has two spring-biased clamping arms, each of which can be rotated about an axis of rotation relative to a frame. These clamping arms are brought into an open position and, after contact with the tibia, are released hereafter by means of a manual release device. Due to the spring preload, they then enclose an ankle joint or the tibia and clamp it. The clamping arms are pretensioned in the closing/clamping direction. The spring preload causes a force-fit fixation of the alignment aid at or immediately above the ankle, which has the disadvantage, however, that hematomas can occur on the patient at the affected body parts due to the clamping force.

The clamping arms exert a spring-loading effect on the ankle joint or ankle. However, the fixation clamp is not adapted to a patient's anatomy, so that the clamping arms exert a different degree of contact force/clamping force depending on the foot/leg shape and the thickness of the ankle joint. This also results in a holding force of the fixation clamp that depends on the shape of the ankle.

Furthermore, a tibia alignment guide of the proximal fixation type is known, for example, from U.S. Pat. No. 7,344,542 B2, in which a transverse beam is rigidly connected to a telescope-type main rod at its proximal end portion. At the free end portion of the transverse beam, fastening pins are mounted which are driven into the tibia for additional fixation of the alignment aid; moreover, a lever is also supported on the transverse beam which, when actuated, presses against the tibia to pull the pins held on the transverse beam out of the tibia. This means that the entire transverse beam together with the integrated pins is levered out against the bone, as a result of which the connection between the tibia cut block or saw gauge and the vertical main rod must be simultaneously released in a disadvantageous manner.

Finally, a surgical nail puller is known in principle from US 2010/0087831 A1, which can reach under a nail head and pull it out of the bone by means of a lever and a transmission.

Tibia alignment aids/alignment devices of the type described above have fundamental problems, particularly with regard to their handling:

- For example, it is necessary to have available alignment aids of different design for the two attachment principles mentioned. This is expensive and complicates the entire handling process including storage, sterilization, etc.
- Furthermore, the alignment aid is often removed from a patient's leg during a surgical procedure. This always requires several manual operations/actions with conventional alignment aids, depending on the fastening principle, for example to loosen the distal and/or proximal fastenings.
- At this point, it should be noted once again that body dimensions are patient-specific and vary considerably. The conventional alignment aids of known design, however, can only cover a limited range of deviation in each case by means of corresponding adjustment options. This means that with the known systems it is not possible to cover the complete, worldwide length spectrum of tibiae in each case, but several systems/alignment aids with possibly overlapping length spectra must be kept in stock, which entails the problems already mentioned above with regard to costs and complicated handling processes. Also, for the adjustment of the varus/valgus alignment, the length of the telescopic rod/main rod that is coarsely adjusted first must always be actively (manually) secured against misalignment. This means that a subsequent fine correction of the length adjustment always requires a manipulation (e.g. temporary manual partial release) of a locking mechanism, which is normally supposed to fix the roughly adjusted length.

Another problem of the prior art is that the fixation to the patient's ankle is usually made in a force-fitting manner or the clamping arms are preloaded in a force-fitting manner, causing an insufficient ability of positioning due to the resulting inherent elasticity of the clamping arms. There is no adaptation to the patient's anatomy. In the worst case, this leads to a detachable fixation, which, however, is not sufficient due to the high requirements for dimensional accuracy or precision on the alignment of the plane of the resection described at the beginning. Also, the different clamping forces of the elastically pretensioned clamping arms can cause, among other things, hematomas on the patient's body parts.

Not all anatomical sizes are covered by the fixation clamps known in the prior art, since the clamping force depends on the respective anatomy of the patient. Therefore, different variants of fixation clamps of the alignment device would have to be manufactured and kept ready for an optimum adaptation, but this is not practiced in practice due to high costs and poor manageability. In the case of alignment device fixation clamps, which are spring-loaded against the ankle, there is the problem that, depending on the shape of the foot and the thickness of the ankle, the contact force exerted by the spring varies.

SUMMARY

It is therefore a fundamental object of the present invention to at least partially avoid or at least reduce the above-mentioned disadvantages of the prior art and, in particular, to provide a (tibia) alignment device which allows efficient handling, in particular a simple, safe and fast fixation as well as simple and fast release of the fixation from a body extremity/body limb/lower leg of a patient, the alignment device being preferably adapted or adaptable for different anatomies of body extremities and being preferably usable for any anatomy and avoiding hematomas as far as possible by its modes of operation and configurations. Also, the alignment device should preferably have a design that is as simple as possible and, if necessary, easy to assemble, clean and sterilize. On the whole, it should also be possible to keep the costs associated with the handling of an alignment device or alignment aid of the type in question as low as possible. Finally, the alignment device should preferably be as flexible as possible in terms of applications.

The alignment device ("extramedullary tibia alignment system") according to the present invention is/forms an extramedullary alignment system, in particular for performing the proximal tibial incision in a total or unicondylar knee arthroplasty (TKA/UKA) according to the rules. It can essentially be used to adjust the saw block, known from the prior art, for the proximal tibial incision to the appropriate landmarks of the tibia according to clinical requirements and the surgeon's conception, and to achieve sufficient stability when attaching the saw block to the anterior epiphyseal region of the tibial bone. Furthermore, if desired by the surgeon, it should ensure a sufficiently high stability also during sawing the bone with the help of the saw block, for example by keeping the alignment device selectively fixed to the tibia.

The present system or the alignment device according to the invention fulfills both different alignment and fixation principles required by the users in one unit. In the following, these are the versions referred to as "anterior fixation" and "proximal fixation". The designation was made according to their primary fixation option as already defined above. According to the invention, the version "proximal fixation" is preferably achieved by placing an additional "proximal fixation unit" (adapter-like) on the version "anterior fixation", thus additionally allowing the proximal fixation to the "Eminentia intercondylaris tibiae". In the case of the "anterior fixation", the primary fixation (as standard) is performed in the proximal region by means of a pin placed in the "Tuberositas tibiae" through an oblong hole in the saw block.

The following parameters are set or aligned with the alignment device according to the invention:

The varus/valgus-cutting angle.

The flexion/extension-cutting angle (posterior/anterior or also dorsal/ventral cutting angle (slope)).

The proximal cutting height (≙thickness of the desired bone section).

The alignment device according to the invention consists essentially of the following components:

Distal retaining clamp, especially foot clamp

The distal retaining clamp (hereinafter referred to only by way of example as a foot clamp) is located at the distal end of the alignment device according to the invention. It fulfills the following functions:

Holding and stabilizing the alignment device in the region of the ankle with regard to lateral and rotational movements relative to the tibia (or relative to the anatomical tibial axis and thus usually also relative to the mechanical tibial axis)

Alignment of the alignment device in reference to the distal landmarks
1. distal anterior ankle center
2. distal tibial anterior edge Adjustability of the following parameters:
1. varus/valgus cutting angle
2. anterior/posterior cutting angle (slope)

Easy and traumatic removal of the alignment device from the patient's leg

Enlargement/reduction of the longitudinal range of the alignment device

Shaft

The (telescopic) shaft is preferably made up of a slide rod and a handle. These two elements are connected to each other like in a telescope. The shaft connects the distal instrument part (foot clamp) with the proximal instrument part (saw block, if necessary an adapter for the saw block and/or an attachment arm for the version with proximal attachment).

The shaft also fulfills the following additional functions:

It supports the alignment of the alignment device with regard to all three parameters mentioned above. This is done by referencing the shaft visually and/or haptically by simultaneously contacting the tibial leading edge (with index finger, middle finger and thumb) and the anterior shaft edge (with the base of the hand between index finger and thumb) to the tibial leading edge.

It preferably includes an arresting unit (hand screw with spring-loaded clamping element, for instance) that is used to secure the set alignment height for the alignment device. In the version "anterior fixation", the height adjustment of the alignment device is set exclusively via this function. For the version "proximal fixation", there is preferably also an adaptively attachable, vertically shiftable carriage to which the saw block is then attached or attachable.

Another function of the arresting unit is to secure the initially estimated and not yet finally determined height setting when aligning the alignment device. This is done by means of a self-locking effect, for example realized with a spring-loaded pin in the arresting unit, which presses against the distal shaft portion of the alignment device. This allows the user to make corrections regarding the alignment of varus/valgus, rotation and height at the same time. The adjustable self-adhesion prevents the alignment device from collapsing due to gravity and thus facilitates handling and expenditure of time, thus having a positive effect on operating time and thus on the surgical team and patients.

The clamping unit can be realized in different versions.

1. By a solution with clamping function and self-adhesive sliding function or
2. With clamping function, self-adhesive sliding function and fully opened with free-falling function.

Adapter for fastening the saw block to the shaft

A preferably provided saw block adapter is located at the proximal end of the alignment device (especially at the handle) and has the following functions.

Accommodating the tibia saw blocks for the right or left leg.

Free gliding arrangement on the shaft, especially in combination with the version "proximal fixation" for the final cutting height adjustment. The use of free gliding is also conceivable with the version "anterior fixation", especially if the adapter is initially fixed in a central position. This allows easier height correction after arresting the fixation unit.

Proximal fixation unit

An optionally arranged "proximal fixation unit" essentially consists of a horizontal cantilever arm and a vertical support column. The "proximal fixation unit", or vertical support column, can be selectively attached to the proximal end of the shaft in the version "anterior fixation". It has the following functions:

Easy fixation and release of the "proximal fixation unit" in the proximal shaft part in the version "anterior fixation"

Horizontal movability of the cantilever arm in the support column, if necessary with self-adhesion, if no to low sliding forces act from outside. The movability of the cantilever arm guarantees that the alignment device is compatible with tibial anatomies worldwide and that the user can set the intended slope at any time.

Securing against rotation and lateral displacement by fixation to the Eminentia intercondylaris tibiae by means of preferably two drive pins.

Releasing the pins with the impact lever.

Guiding the saw block adapter during cutting height adjustment.

Adjustable cutting height feeler

The cutting height feeler can be selectively attached to the proximal tibia saw block and essentially consists of the following elements:

Adapter interface to the tibia saw block with lock-and-release mechanism

Self-retaining, sliding contact arm with contact tip

Unit for height adjustment

The adjustable cutting height feeler has the following functions:

Easy assembly and disassembly of the cutting height feeler to the tibia saw block(s).

Scanning of a bony landmark with the contact tip. The landmark selected by the user is the reference relative to which the cutting height is set.

Horizontal movability of the height feeler to adapt to the different anatomies of the epiphyseal tibia and to reach the medial and lateral tibial condyle from the same adapter site.

Adjustment of the cutting height

Proximal tibia saw block

There are preferably different variants of tibia saw blocks. The variants differ in the following features:

Applicable for the right and left tibia

Adapted to the two versions "anterior fixation" and "proximal fixation".

The saw blocks have the following function or functional elements:

Guidance of the saw blade for the bone section

Holes for attaching the saw block to the bone and for correcting the cutting height up to +4 mm Adapter interface for mounting on the alignment device/shaft via the (saw block) adapter Adapter interface for mounting the cutting height feeler The above objects of the invention are described in more detail below:

A first gist of the present invention includes, inter alia, providing an alignment device, in particular for a tibial resection guide, with a telescopically extendable shaft (telescopic device), which can be equipped/is equipped with a saw block at its proximal end region and has a type of (foot) shackle device, in particular a clamping device, at its distal end region, which comprises at least two pivoting clamping elements/clamping arms acting against one another for clamping the distal end of, for example, a tibia of a patient, the clamping elements of the clamping device being each of arcuate design and aligned with one another in such a way that, viewed in the direction of the longitudinal axis of the alignment device/shaft, they form between them an oval-shaped region which is designed for receiving the distal region of the tibia in a clamping manner. According to the invention, the clamping elements are each designed to be resilient or are made of a resilient material, so that the clamping device of the alignment device can be removed from the tibia preferably with one hand by utilizing the spring properties of the clamping elements.

In other words, the clamping device arranged at the distal end portion of the alignment device or of the telescopic/extendable shaft has a preferably Y-shaped tibia contact block consisting, among other things, of two essentially V-shaped diverging, rigid contact arms (forming a carriage), to the respective free end regions of which the resiliently bendable/yielding clamping arms are pivotably articulated, which in turn are each preformed in an arc shape in the closing-pivoting direction/clamping direction. If the clamping arms formed in this way are pivoted towards each other in clamping direction (foot clamp closed), the above-mentioned oval clamping shape results in top view, as a result of which a tibia clamped by it in the ankle region of a patient is simultaneously subjected to force almost along the entire circumference of the clamp, in particular from behind, laterally and from the front.

Due to the resilient design of the clamping elements, they are also attached to the distal end of the tibia in a way that is gentle on the tissue, i.e. atraumatic, with high translational and rotational stability. When reference is made to the lower end of the tibia, this refers to the region of the lower tibial third including the ankle joint directly up to the contact of the dorsum of the foot.

The alignment device or the ankle shackle device (foot clamp) further preferably comprises a ratchet mechanism via which the clamping elements are each supported on the tibia contact block of the ankle shackle device and by means of which the clamping elements can be pretensioned independently of one another with different pretensioning forces.

Due to the spring elasticity, the clamping elements advantageously have elasticity and at the same time a high holding force and high rotational and translational stability against unintentional adjustment of the entire alignment device. This high stability is achieved by the fact that the clamping elements are closed and additionally held by the ratchet mechanism.

Furthermore, the two clamping elements interlace at their respective free ends when the foot clamp is closed. Due to this interlacing, it is advantageously possible to simultaneously apply a lateral holding force and a holding force coming from lateral posterior direction. In this way, a high areal closing and holding force is applied multidimensionally to the tibia in an advantageous manner.

In a particularly advantageous manner, this holding force is constant for all anatomical circumferential sizes of the tibia, since the resilient clamping elements are only stressed when they come into contact with the tibia. The clamping elements thus advantageously fulfill a dual function, as the compressive force to hold the tibia is only applied when the tibia contacts the clamping elements.

According to a further preferred embodiment, the clamping elements are additionally each fork-shaped in design and the prongs of the respective fork are arranged offset from one another in such a way that, in the closed state (closed foot clamp), they engage one another in overlapping manner so that the tibia is held firmly. The clamping elements thus effect simultaneous gripping and holding of the tibia from behind, laterally and from the front. Configuring the clamping elements in a fork shape allows them to interlace in the posterior region of the tibia and thus press the latter against the contact block. In a particularly advantageous manner, the clamping elements are designed in such a way that they interlace in the region of the ankle joint.

Preferably, the respective tips of the prongs are shaped opposite to the respective arc shape of the clamping elements, so that the removal process from the tibia occurs without any injury. The fact that the clamping elements are curved in their end region means that they can be pulled off the tibia in a very tissue-friendly manner (without first having to open the ratchet mechanism), while it is advantageously prevented or reduced that the ends cut into the tissue.

A second gist of the present invention is that the telescopic device, i.e. the telescopic shaft in its proximal region, preferably in addition to the foot clamp described above, comprises a decoupling device, i.e. a saw block adapter (may also be referred to as a decoupling device), which is designed to separate/uncouple the saw block from the telescopic device or the shaft upon (manual) activation/release. In this way, it is easily possible to disconnect the alignment device/alignment aid, i.e. the telescopic shaft, from the cutting/saw block with virtually one manual operation. In a preferred case, if the foot clamp is designed according to the first main idea of the present invention described above, the clamping elements can be easily pulled off the distal tibia (also with one hand) due to their inherent elasticity under resilient spreading (and without opening the foot clamp at the ratchet mechanism), so that the alignment device as a whole can be removed with a single movement.

In other words, advantageously, due to the constructional design of the foot clamp and the proximal saw block adapter/adapter interface, the telescopic shaft (or the alignment aid) can be pulled off the patient's tibia in a tissue-gentle manner, i.e. in a non-traumatic manner, and in one simple (single) operating action.

The decisive factor here is that the retaining elements of the foot clamp are designed to be sufficiently elastic so that they can be easily removed from the distal tibia without the need to operate a release mechanism, and that at the same time they exhibit sufficiently high rotational and translational stability against unintentional adjustment of the alignment device. In addition, it is advantageous for this case that the decoupling device, i.e. the adapter interface, for the tibia saw block is designed in such a way that the handle for releasing (preferably a lever or release button) the alignment device from the saw block can be actuated with a simple thumb pressure so that the shaft can be grasped by the associated whole hand. With the alignment device comprising the described devices and elements, it is thus possible, after attachment of the saw block to the bone and after operating the release button by thumb pressure, to remove the alignment device from the patient's tibia with one hand without the need for any further operating action.

According to a preferred embodiment to the second main idea of the present invention, the telescopic device and/or the telescopic shaft has in its proximal region a handle which is designed in such a way that it can be grasped by one hand and that the decoupling device/saw block adapter for activation has a pressure element above the handle, which pressure element is preferably arranged at an angle A of between 90° and 150°, more preferably at an angle of between 95° and 120° and in particular at an angle A of 100° to the longitudinal axis of the telescopic device, so that the pressure element can be activated by the thumb of the one hand.

The arrangement of the pressure element at the preferred angle A of 100° creates a position of the pressure element that is particularly easy to reach. Thus, the pressure element can be advantageously triggered with a single thumb pressure and the alignment device can be removed from the tibia by a single hand of the operator. Advantageously, this prevents additional hand movements or procedural steps, making the alignment device removable in a single motion.

More specifically, the saw block adapter is designed on the side of the shaft as a male adapter interface approximately in the manner of a plug, for example with two peg-shaped protrusions, on which a clamp or retaining bracket is preferably mounted in a rocker-like manner. The retaining bracket forms at least one engagement undercut (e.g. latching hook) at its one end portion, whereas the pressure element for manual pivoting of the retaining bracket preferably in the release direction is arranged at its other end portion.

Accordingly, a female adapter interface, such as in the manner of a socket with e.g. two (blind) bores, is arranged/designed on the saw block, which can be engaged by the plug in particular in a torque-proof manner, this engagement being secured by means of the retaining bracket, for example by engaging behind retaining edges on the side of the saw block. It should be expressly noted at this point that the male adapter interface can of course also be provided on the side of the saw block and the female adapter interface on the shaft.

Preferably, the saw block adapter is formed as a separate (independent) component comprising a docking point to which the adapter can be firmly connected with handle preferably at its proximal end. Further preferred, the saw block adapter has a vertical through hole such that the one part of the telescopic shaft (slide rod element, on which the foot clamp is distally arranged) can slidingly (completely) penetrate both the handle and the adapter.

Further, according to a third inventive main idea, the present invention consists in providing an alignment device for a tibial resection guide, comprising the following components:

- a clamping device (foot clamp) for clamping the distal end of a tibia of a patient preferably according to the first main idea of the invention;
- a tool guiding device/saw block for guiding a tool/saw during resection of the tibia,
- a telescopic device/telescopic shaft preferably according to the second main idea of the invention, which is connected to the tool guiding device/saw block and to the clamping device and which is designed to align the devices with respect to the tibia, the telescopic device comprising a handle element or handle designed to receive a slide rod element movably mounted therein (with clamping device distally arranged thereon), the telescopic device comprising a (manually adjustable) securing element which is arranged between the handle and the slide rod element and which can be (manually) adjusted to reach a first position in which a first compressive force is brought about between the handle and the slide rod element, and which can additionally be adjusted to reach a second position in which a second compressive force is brought about between the elements which differs from (is larger than) the first compressive force.

Thus, a securing element is provided which is connected to the telescopic device and which is designed to be arranged between the handle and the slide rod element and which can generate a first and a second compressive force between the handle and the slide rod element. By providing two different compressive forces between the elements, the telescopic device is readily adjustable and operable depending on the requirements of the treating physician.

A preferred embodiment is provided in that, in the first position, the (first) compressive force generated thereby causes a self-locking effect between the handle element and the slide rod element in a vertical arrangement of the alignment device, i.e. in the longitudinal direction of the telescopic shaft, and in that, in the second position, the (second) compressive force generated thereby causes the elements to be fixed relative to one another.

In the first position, therefore, a merely self-locking slide rod is advantageously effected, the self-locking effect being at least sufficient to prevent a relative displacement of handle and slide rod element due to gravity, and in the second position a fixing of the slide rod in the handpiece is additionally effected by means of the securing element. The fixation, for example by means of frictional clamping, is advantageously achieved by screwing the securing element, i.e. an arresting/fastening screw, in as far as to the limit stop. The self-locking release of the slide rod for its axial movability in the handle is achieved by incorporating a spring-loaded pin in the securing element, i.e. in the arresting/fastening screw, which generates a frictional connection by means of a (spring-force-dependent) clamping force between the handle and the slide rod when the screw is partially to fully open. This clamping force is designed such that the generated static friction counteracts gravity, with the acting mass being significantly influenced by the elements attached to the proximal and/or distal end of the alignment device. Advantageously, the clamping force has the effect that the treating physician or user is able to release the elements for height adjustment at any time and the set height is maintained. The alignment device thus advantageously does not collapse, as would be expected due to gravity. This allows the user to readjust the height at any time while being able to concentrate on the adjustment of the other parameters, e.g. varus/valgus and/or slope. On the whole, this facilitates the workflow during treatment in a beneficial way. Only when the (rough) height adjustment has been completed, the arresting/fastening screw is screwed in as far as to the limit stop, as a result of which the spring effect is neutralized and a clamping force is applied between the handle and the slide rod (element) as a function of the screw-in force, which is much higher than the spring force previously applied and ultimately clamps the two elements firmly against each other.

In a further preferred embodiment, the securing element is additionally adjustable in such a way that in a third position a third compressive force acts between the elements, which is designed in such a way that in a vertical arrangement of the alignment device the elements (handle, slide rod) automatically slide into each other due to the applied gravity. In this third position, a free-falling slide rod is thus provided.

This is achieved, for example, by the fact that the clamping pin of the securing element no longer generates any static friction or only a low/negligible static friction, which in turn is caused by the fact that—when the fastening screw is fully opened—the force of the spring acting on the clamping pin is so low that the static friction described is no longer relevant and there is only a sliding friction between the clamping pin and the slide rod.

A further, fourth main idea of the present invention is to provide an alignment device for a tibial resection guide comprising the following components:

- a clamping device (ankle shackle) preferably according to the first main idea of the invention for clamping the distal end of a tibia of a patient;
- a tool guiding device/tibia saw block for guiding a tool during the resection of the tibia,
- a telescopic device/telescopic shaft preferably according to the second and/or third main idea of the invention, which is connected or can be connected to the tool guiding device and to the clamping device and which is designed to align the devices with respect to the tibia, wherein the tool guiding device has a seating recess/docking/adapter interface designed to releasably receive a height sensing element or cutting height feeler (adjustable contact element) for sensing/fine adjustment of the resection height.

According to the above embodiment, the cutting height feeler is selectively attached to the proximal tibia saw block and consists essentially of the following elements:

- An adapter interface to the tibia saw block preferably with latching and releasing mechanism
- If necessary, a self-retaining but sliding contact arm with contact tip
- A unit for (manual) height adjustment The (adjustable) cutting height feeler has the following functions:

Simple assembly and disassembly of the stylus to the individual tibia saw blocks, which may be designed so as to differ from each other (e.g. for left and right leg)

If necessary, a spring-loaded latching mechanism is attached to the distal end of the stylus, which arrests the stylus in place after the stylus has been introduced/inserted into holes/seating recesses/docking points provided for this purpose in the tibia saw blocks. The stylus remains rotatable around the insertion axis relative to the respective saw block.

The optional axial arresting is achieved, for example, via a "spring-loaded nose" that is pushed back laterally during insertion due to the beveled distal contact surface and locks in place in a groove in the tibia saw block when fully inserted into the tibia saw block.

The "spring-loaded nose" can be released from the arresting position by means of a lever, which pulls the nose back against the spring when operated, thus releasing the lock. In this state, the stylus can be easily removed from the saw block.

Scanning a bony landmark with the contact tip. The landmark selected by the user is the reference against which the cutting height is set.

The landmark is detected with the contact tip, which is attached to the posterior end of the contact arm. Due to the fineness of the contact tip, very small bony structures can be detected visually very well and accurately by means of eye control.

Horizontal movability of the height feeler to adapt to the different anatomies of the epiphyseal tibia and to reach the medial and lateral tibial condyle from the same adapter site.

With the help of the preferably rotatable stylus and the contact arm which is preferably movable along its main axis, any bony landmark on the proximal surface of the tibial condyles can be reached. In this context, the dimensions of the contact arm are designed such that the worldwide anatomy (of Asians, Caucasians, etc.) is taken into account.

In order to maintain the desired extended length of the contact arm, the contact arm can be secured against axial displacement, e.g. in self-locking manner by means of a frictional engagement.

Adjusting the cutting height

By latching the stylus in place in the tibia saw block and due to a defined stop of the stylus on the saw block, the distance of the contact tip of the stylus is determined in relation to the lower edge of the saw slot in the saw block.

The set cutting height is indicated by numbers, for example, on the circumference of a screw head of the adjustable height feeler. The number indicating the set height is preferably indicated by a pointing element at the anterior end of the holding unit of the contact arm.

The adjustment of the tibial section thickness from 0 to 16 mm (or 0 to 14 mm) is achieved with preferably only one turn of the screw head. In this case, the height is adjusted by means of a spiral in a guide element of the screw head. A stop element at the upper end of the guide element can be provided, if necessary, to prevent the screw head from being completely unscrewed from the stylus.

Final adjustment of the cutting height and alignment of the alignment device for the proximal tibia cut:

After setting the desired cutting height, the stylus is moved against the landmark selected by the user and the alignment device is aligned. The landmark is approached by moving the handle together with the mounting elements/saw block adapter on the slide rod. Once the alignment device is aligned in height and varus/valgus and slope are aligned as desired by the user, the saw block is finally firmly anchored to the bone with a fixation pin through the fixation holes provided for this purpose in the saw block. After this, at least the stylus must be removed in order to be able to perform the tibial saw cut.

The height sensing element, which is also referred to here as the cutting height feeler, can be attached to the proximal tibia saw block, as explained above. By using the height sensing element, the distance of the contact tip of the height sensing element relative to the lower edge of a saw slot of the tool guiding device/saw block is defined in an advantageous manner. The contact tip of the height sensing element advantageously allows very fine bony structures to be detected very precisely by means of eye control. On the whole, the height sensing element achieves a particularly precise alignment of the entire alignment device.

In a preferred embodiment, the seating recess is a (blind or through) bore extending from the top side of the tool guiding device/saw block along the longitudinal axis of the alignment device/shaft, the height sensing element having an insertion element/peg comprising a latching mechanism, which can be inserted into the seating recess in a latching manner.

At the distal end of the height sensing element (which is also referred to as stylus), i.e. at the distal (free) end/end portion of the insertion element/peg, the spring-loaded latching mechanism is attached, which locks the stylus in the seating recess of the saw block. Advantageously, the stylus remains rotatable about the insertion axis, allowing easy alignment of the sensing element.

In a more preferable embodiment, the latching mechanism is preferably arranged in the insertion element itself and comprises a detent nose which, in the inserted state, engages behind the seating recess in such a way that the height sensing element is axially retained therein.

The axial arresting is advantageously achieved by means of a "spring-loaded nose" which, when the stylus is inserted, is automatically pushed back laterally due to its beveled distal contact/sliding surface and, when fully inserted into the tool guiding device, latches in place in an undercut in the tool guiding device. The "spring-loaded nose" can additionally be retracted by hand and laterally from the arresting position against its spring bias by means of a lever or an actuating button, thus cancelling the latching engagement. In this state, the stylus can be easily removed in an advantageous manner from the tool guiding device, i.e. from the saw block.

Furthermore, a fifth inventive idea of the present invention is to provide an alignment device for a tibial resection guide, preferably comprising the following components:

a clamping device (ankle shackle) preferably according to the first inventive idea of the present invention for clamping the distal end of a tibia of a patient;

a tool guiding device/saw block for guiding a tool during the resection of the tibia;

a telescopic device or telescopic shaft preferably according to at least one of the second to fourth main ideas of the invention, which is connected or can be connected to the tool guiding device at its proximal end portion and is connected or can be connected to the clamping device at its distal end portion, and is designed to align the devices with respect to the tibia, the telescopic device having in its proximal region a drive device mount for selectively receiving a proximal fixation unit or drive device, which is formed by the shaft, at least partially designed as a hollow body, of the telescopic device, preferably slide shaft/slide rod element.

As already mentioned above, the alignment device according to the invention is converted from one solution variant to a second one by a simple instrumental addition. The two variants are the "anterior fixation" and the "proximal fixation".

The conversion is solved by placing an additional "proximal fixation unit", namely the drive device, on top of the version "anterior fixation", thus allowing to apply the proximal fastening (version "proximal fixation") to the "Eminentia intercondylaris tibiae".

The "proximal fixation unit" essentially consists of the horizontal cantilever arm including the drive pin unit and of the vertical support column including the lever mechanism for clamping the unit to the alignment device or the shaft, in particular the slide shaft element. The "proximal fixation unit" is attached to the proximal end of the alignment device in the version "anterior fixation". It has the following functions:

- Easy fixation and release of the "proximal fixation unit in the proximal part of the version "anterior fixation"
  - The fixation is preferably performed by a lever-spread-mechanism.
  - By actuating a lever (thumb pressure downwards), a rod is moved upwards within the support column.
  - For this purpose, the rod is guided in a hole in the distal shaft part (support column) of the "proximal fixation unit".
  - At the distal end of the rod, a square element, beveled proximally by e.g. 45°, is firmly attached.
  - Said square element abuts the distal end, e.g. also beveled by 45°, of the shaft of the "proximal fixation unit", which preferably has the identical square shape as the square element on said rod.
  - Both square elements form the unit which is inserted into the square shaft tube of the proximal end of the version "anterior fixation" (in the region of the handle).
  - The preferred 45° bevels of the two square elements are arranged to be mirror-inverted to each other.
  - If the more distally arranged square element is now pulled toward proximal by the lever mechanism and the rod, a lateral offset of said two square elements occurs due to the 45° bevels arranged in reverse manner.
  - If this occurs when both elements are in the square tube, a clamping and thus a fixation of the "proximal fixation unit" in the proximal end (in the square tube) of the shaft of the alignment device in the version "anterior fixation" will inevitably occur.
  - By opening said lever mechanism, the clamping is released and the "proximal fixation unit" can be removed in its entirety from the alignment device with only one manual operation. The lever for releasing is moved upwards with fingers (preferably the middle finger and/or ring finger) when gripping the "proximal fixation unit.
- Horizontal movability of the cantilever arm in the support column with self-adhesion, if no to low sliding forces act from the outside.
  - The movability of the cantilever arm guarantees that the alignment device is compatible with tibial anatomies worldwide and that the user can therefore set his intended slope at any time.
- Securing against rotation and lateral displacement by fixation to the Eminentia intercondylaris tibiae using preferably two drive pins.
- Loosening of the pins is performed with an additional impact lever, if necessary
- Guiding the saw block or saw block adapter in the longitudinal direction of the shaft during the cutting height adjustment.
  - For the height adjustment of the saw block, the tibia saw block adapter, attached to the proximal end of the alignment device version "anterior fixation", must be released for axial sliding along the telescopic shaft and independently from the handle.
  - The release is achieved by actuating a corresponding locking mechanism to release the coupling between the saw block adapter and the handle. For example, the locking mechanism (pushbutton) is attached laterally on the proximal end of the alignment device.
  - The sliding knob assumes 2 positions in its function:
    1. Position: Locking the tibia saw block adapter-≙"anterior fixation"
    2. Position: Release of the tibia saw block adapter-≙"proximal fixation"

Advantageously, the alignment device is consequently converted from one solution variant to a second one by a simple instrumental addition, being the "anterior fixation" and the "proximal fixation unit" as defined above.

Further advantageously, the drive device can be inserted at its distal end into the hollow body of the shaft, i.e. into the at least partially hollow and proximally open slide shaft element of the telescopic device, in such a way that clamping of the drive device in the hollow body/slide shaft element can be effected via said clamping mechanism. Thus, positive connections such as bolts, screws, etc. are preferably dispensed with, and only frictional connections are employed that can be made quickly and easily.

According to a sixth main idea, the present invention preferably consists in providing an alignment device for a tibial resection guide, comprising the following components:

- a clamping device preferably according to the first main idea of the invention, comprising at least two clamping elements acting against one another for clamping the distal end of the tibia of a patient, which are attached to a cantilever designed to be inserted into a foot clamp reception device,
- a tool guiding device for guiding a tool during the resection of the tibia,
- a telescopic device preferably according to at least one of the second to the fifth main idea of the invention, connected to the tool guiding device and to the clamping device and designed to align the device with respect to the tibia, the telescopic device having a handle element designed to receive a slide shaft/slide rod element slidably mounted therein, the alignment device comprising a first slide shaft element/slide rod element having a first length and a second slide shaft element/slide rod element having a second length, the respective slide rod elements being provided to be inserted into the handle element as required, wherein the respective slide rods are connected, at their distal end, preferably perpendicular to the foot clamp reception device, and the ratio of the first length of the first slide rod element to the second length of the second slide rod element is preferably between 1 and 1.5, more preferably between 1.1 and 1.3 and in particular is equal to 1.27, the length being measured in each case from the proximal end of the slide rod to the center of the foot clamp reception device, so that different lengths of the tibia can be resected by each of the first and second slide rods.

In other words, the sixth main idea of the present invention relates to the general creation of possibilities for changing the length spectrum of an alignment device as cost-effectively as possible, preferably in accordance with at least one of the first to fifth main ideas of the invention in the context of a single alignment device. There are essentially two measures available for this purpose, which can be taken together or independently of each other:

Firstly, there is the first possibility of providing an alignment device of the present type with a telescopic (extendable) shaft or a telescopic device, on the proximal end portion of which a saw block is mounted or can be mounted and on the distal end portion of which a clamping device or foot clamp is arranged or can be attached. According to the invention, the extendable shaft or telescopic device has a slide shaft element/slide rod element (or simply slide rod), which is received in a handle in an axially movable manner and can preferably be fixed relative to the handle in a selected/selectable extension position by means of an arresting device (arresting screw). According to the invention, this alignment device comprises a set of slide rods/slide shaft elements of different shaft/rod lengths (at least two slide rods with rod lengths that differ from each other), which are selectively interchangeable and can be inserted telescopically into the handle in a selected manner.

In an advantageous manner, different lengths of the tibia, i.e. different leg lengths, can thus be resected. This is achieved by replacing the slide rod, which is available in different lengths as a part of the available set of slide rods. Thus, all lengths of the tibia can be resected in an advantageous manner using the alignment device.

Furthermore, the second possibility (which can be used separately or in combination with the above first possibility) is that the clamping elements of the foot clamp reception device are attached to the cantilever arm in a longitudinally offset manner, with the cantilever arm being able to be inserted into the foot clamp reception device in a first position and in a second position by rotating it through 180° degrees, such that in the first position the clamping elements are aligned relative to the distal end of the alignment device and in the second position the clamping elements are aligned relative to the proximal end of the alignment device, so that a height offset of the clamping elements in the longitudinal direction is effected when the cantilever arm is inserted into the foot clamp reception device rotated by 180° degrees from the first to the second position.

In other words, there is preferably provided an alignment device of the present kind with a telescopic (extendable) shaft or telescopic device, on the proximal end portion of which a saw block is mounted or can be mounted and on the distal end portion of which a clamping device or ankle shackle device is arranged or can be attached. According to the invention, the extendable shaft/telescopic device has a slide shaft element/slide rod element (or simply slide rod), which is received in a handle in an axially movable manner and can preferably be fixed relative to the handle in a selected/selectable extension position by means of an arresting device (arresting screw). At the distal end portion of the telescopic device, in particular of the slide rod element, a receptacle/support for mounting/attaching the clamping device/ankle shackle device is provided for this purpose.

The clamping device/ankle shackle device has an ankle shackle portion, preferably a Y- or V-shaped tibia contact block or mounting block (as preferably already described with respect to the first main idea of the invention), on which (the) clamping elements are preferably mounted according to the first main idea of the invention, the ankle shackle device further having a coupling portion, preferably an insertion rod, which can be brought into engagement with the receptacle on the side of the slide rod.

According to the invention, the ankle shackle portion, in particular the clamping elements and/or the tibia contact block, is/are arranged asymmetrically with respect to the coupling portion, in particular with respect to the insertion rod, i.e. arranged to be offset in the longitudinal direction of the telescopic device, in such a way that the ankle shackle portion, in particular the clamping elements, are arranged either above (proximal) or below (distal) the coupling portion (as viewed in the direction of the shaft), depending on the direction of rotation of the coupling portion, when the coupling portion is inserted/engaged in/with the shaft-side receptacle. In this way, the distance between the proximal saw block and the ankle shackle portion, in particular the clamping elements, can be made larger or smaller as desired (depending on the asymmetry/longitudinal offset) by means of a corresponding rotational orientation of the coupling portion during its assembly.

In a particularly preferred embodiment, the height offset of the foot clamp reception or insertion device is measured from the center of the foot clamp reception device to the respective edge point of the clamping elements. In the first position towards the distal end, this distance is preferably between 10 mm and 20 mm and in particular is equal to 15 mm. By the possibility of turning the foot clamp reception device by 180°, an additional length adjustability in both directions, preferably by 15 mm, is achieved. On the whole, the combination of the different lengths of the slide rods with the reversible foot clamp reception or insertion device provides an alignment device which is very flexible in the adjustment of the length and which can thus be used for the worldwide tibia sizes.

BRIEF DESCRIPTION OF THE DRAWINGS

The present invention is explained in more detail below by means of preferred embodiments with reference to the accompanying drawings.

FIGS. 47-51 show detail views of the drive device according to the invention.

The drawings are merely schematic in nature and are intended only to aid understanding of the invention. Identical elements are provided with the same reference signs. The features of the various embodiments can be interchanged.

DETAILED DESCRIPTION

Figure 1:
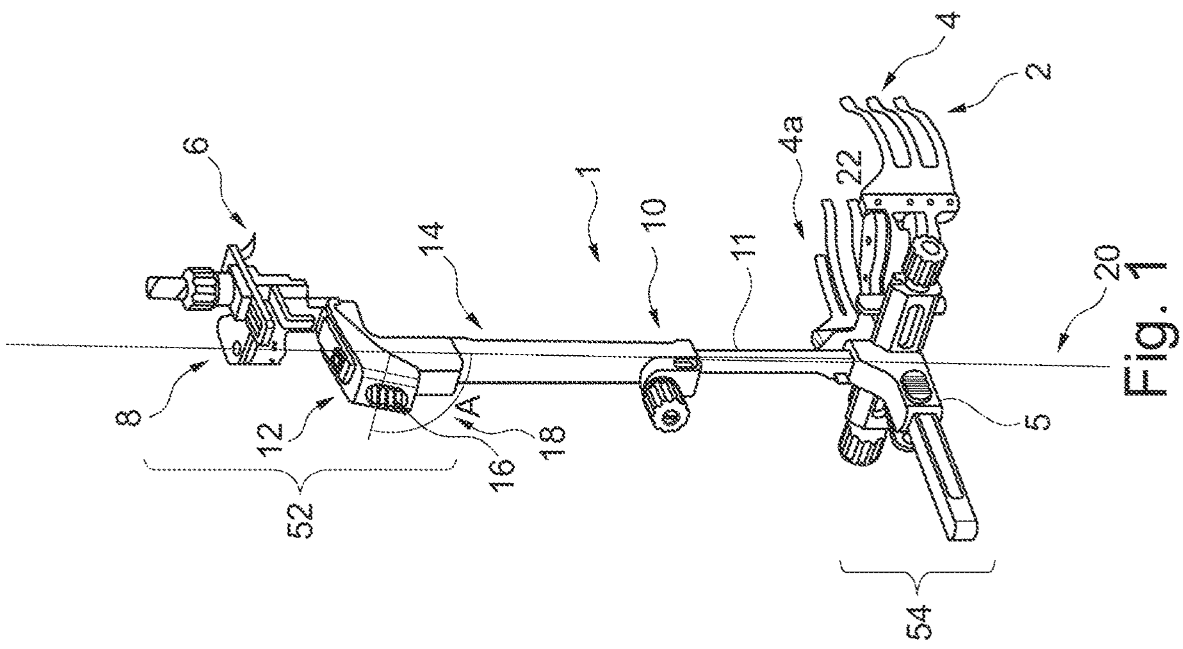
FIG. 1 shows a perspective view of an alignment device of the invention according to a first preferred embodiment.

FIG. 1 shows an alignment device preferably in the form of an extramedullary tibia alignment device 1 according to the present invention in an "anterior fixation version" comprising a proximal region 52 and a distal region 54. The proximal region 52 is defined as the region facing towards the patient's body, and the distal region 54 is defined as the region facing away from the patient's body. The distal region 54 is therefore the region where, for example, the patient's foot/ankle is located.

Accordingly, the alignment device 1 comprises/has, among other things:

- a telescopic device 10, which forms the central part of the alignment device 1 and has a proximal handle 14, a (telescopic/extendable) distal slide shaft element 11 supported so as to be axially movable in the handle 14, and a distal receptacle/connection point 5 for an ankle shackle/clamping device 2,
- a distal ankle shackle/clamping device 2 which is insertable (is inserted) into the distal receptacle 5 or can be engaged with it,
- a proximal (mounting) saw block adapter/decoupling device 12, which is releasably coupled/can be releasably coupled to the handle 14 preferably at the proximal end face thereof,
- a saw block/tool guiding device 8 releasably coupled to the saw block adapter 12, and preferably
- a contact device (adjustable height feeler/contact device) 6, which is releasably coupled to the saw block 8 at the distal side thereof.

In the distal region of the alignment device 1, the clamping device 2 is arranged, which includes/comprises clamping elements 4 and 4*a*, which are arcuately shaped and thus form an oval-shaped region 22 between them, which is provided to clamp or hold the tibia. The telescopic device 10 extends along a longitudinal axis 20. In the proximal region of the telescopic device 10, the handle 14 is arranged, at the distal end/end portion of which the saw block adapter/decoupling device 12 is connected/arranged thereto (directly or indirectly) and thus selectively forms a unit with the handle 14. Provided on the saw block adapter 12 is an actuating/pressure element 16 which is preferably arranged/aligned at an angle A to the handle 14. Hence, said pressure element points in the direction toward the proximal region 52 (upwards), so that a treating physician can enclose the handle 14 with the fingers of one hand and simultaneously operate the pressure element 16 with his thumb. In the proximal region 52, the saw block (also to be referred to as a tool guiding device) 8 is arranged, to which the contact device 6 is detachably attached. The pressure element 16 acts on the decoupling device (saw block adapter) 12, which is provided to separate the telescopic device 10 from the tool guiding device (saw block) 8. As soon as the tool guiding device 8 is firmly connected to the tibia, it can be decoupled from the telescopic device 10 by triggering the decoupling device 12 via the pressure element 16.

Figure 2:
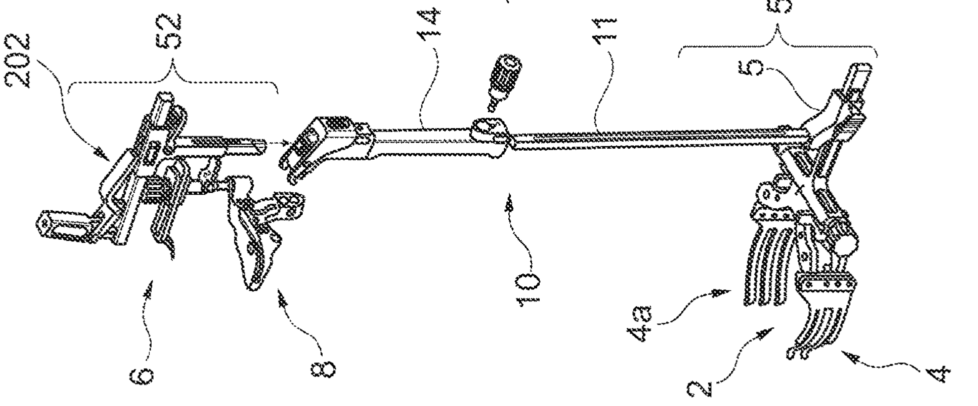
FIG. 2 shows a perspective exploded view of a second preferred embodiment of FIG. 1.

FIG. 2 shows the alignment device 1 in a "proximal fixation version" in exploded view.

In accordance with FIG. 1, the alignment device 1 has in its central part the telescopic device 10, which in its proximal region 52 is in turn connected/connectable to the tool guiding device/saw block 8 via the saw block adapter 12, to which the contact device 6 is attached/attachable. Furthermore, a drive device 202 is additionally attached/attachable to the telescopic device 10 (in adaptive/selective manner). In the distal region 54, the clamping device 2 comprising the clamping elements 4, 4*a* is attached/attachable to the telescopic device 10. In this respect, the alignment device 1 according to FIG. 2 corresponds conceptually to that according to FIG. 1, with the difference that the drive device 202 is additionally mounted on the telescopic device 10 at the proximal end portion thereof.

Figure 3:
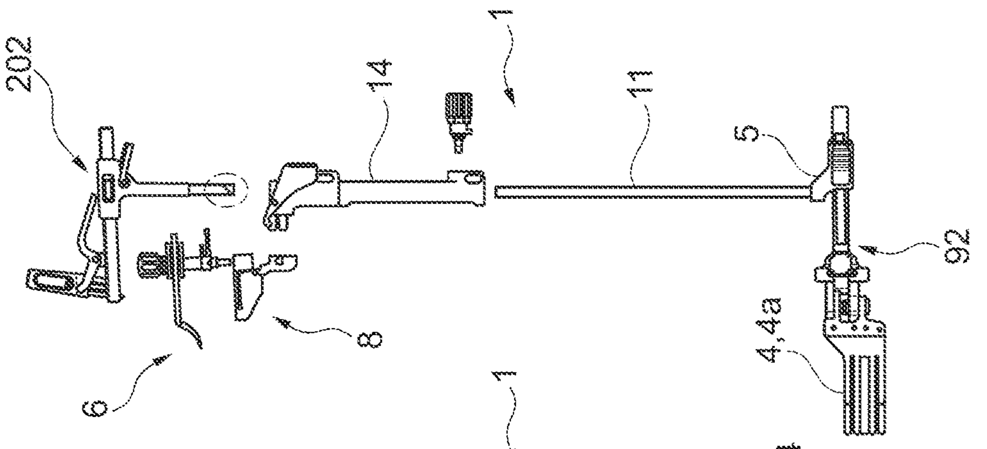
FIG. 3 shows a side view of the alignment device of FIGS. 1 and 2.
Figure 4:
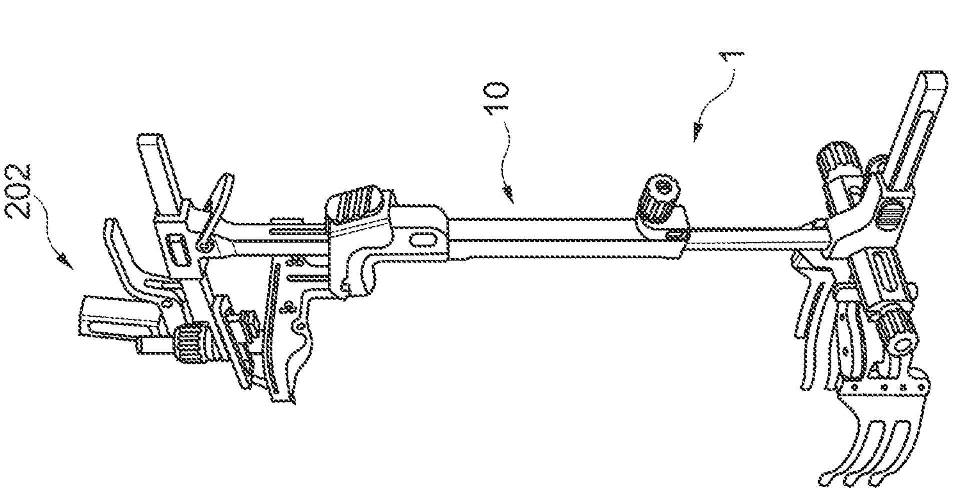
FIG. 4 shows a perspective view of an alignment device of the invention according to a further preferred embodiment.

FIG. 3 shows the alignment device 1 according to FIG. 2 in a side view as well as in an exploded view, and FIG. 4 shows the alignment device 1 in a fully assembled state. In particular in the illustration according to FIG. 3, the individual interfaces on the alignment device 1 according to the invention are at least partially recognizable. Accordingly, the saw block 8 can be selectively engaged with the saw block adapter/decoupling device 12, the contact device 6 can be selectively engaged with the saw block 8, and the drive device 202 can be selectively engaged with the telescopic device 10 and, in particular, the distal slide shaft element 11 at its proximal end/end portion, which for this purpose penetrates the handle 14 axially toward proximal (completely). In FIG. 4, it is shown how the drive device 202 is inserted into the proximal end portion of the slide shaft element 11.

Figure 7:
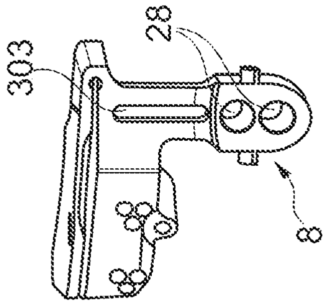
FIG. 7 shows a perspective frontal view of the tool guiding device of FIG. 5.
Figure 10:
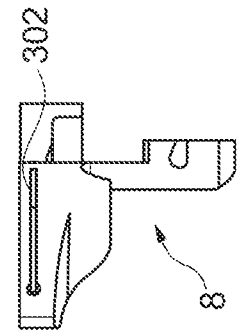
FIG. 10 shows a perspective frontal view of the second embodiment of the tool guiding device of FIG. 8.
Figure 6:
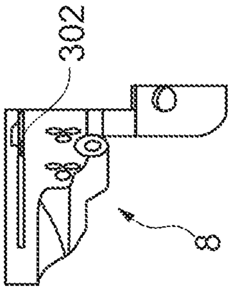
FIG. 6 shows a perspective side view of the tool guiding device of FIG. 5.
Figure 9:
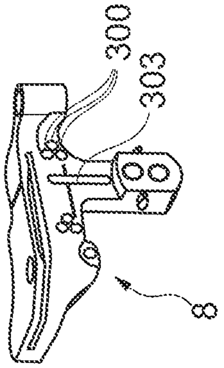
FIG. 9 shows a perspective side view of the second embodiment of the tool guiding device of FIG. 8.
Figure 5:
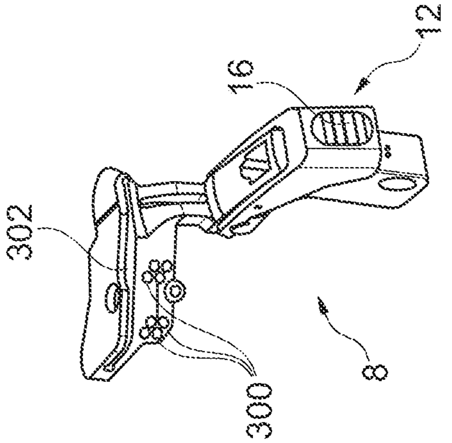
FIG. 5 shows a perspective view of a tool guiding device.

FIG. 5 to FIG. 10 show different views of the tool guiding device/saw block 8 and of the saw block adapter/decoupling device 12. In FIG. 5, the tool guiding device 8 is shown together with the decoupling device 12, which includes the pressure element/pushbutton 16. The tool guiding device/saw block 8 preferably has lateral drive holes 300 that can be used to fix the saw block 8 to the tibia by screws or nails. The tool guiding device/saw block 8 is designed to receive a tool/saw for resection of the tibia in guiding manner, for which a tool guide slot/saw slot 302 is formed in the saw block 8. FIG. 6 shows the tool guiding device 8 with the tool guide slot 302 aligned in the horizontal direction when fixed to the tibia, in a state separated from the saw block adapter 12. FIG. 7 shows the tool guiding device 8 with a female coupling portion, in the present case with two vertically spaced receiving holes 28 and an additional drive slot 303, which is provided to receive fasteners or nails for driving into the tibia.

The tool guiding device, i.e. the saw block 8, has following functions or functional elements:

- Guiding a saw blade for the bone section within the guide slot 302,
- Providing drive/fixing holes 300 and/or the drive slot 303 for fastening the tool guiding device 8, i.e. the saw block, to the bone and, if necessary, for correcting the cutting height by up to +/−4 mm,
- Providing an adapter interface (female coupling portion with receiving holes 28) for mounting on the alignment device/telescopic device 10, and
- Providing an adapter interface for mounting the contact device/cutting height feeler 6.

Figure 8:
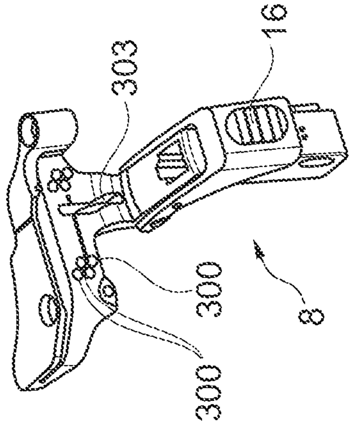
FIG. 8 shows a perspective view of a second embodiment of the tool guiding device.

In addition, FIGS. 5 and 8, for example, show different versions for a saw block 8 according to the invention, namely a version (FIG. 5) for an “anterior fixation variant” and a version (FIG. 8) for a “proximal fixation variant”, in which the adapter interface (insertion hole) for the cutting height feeler 6 is offset with respect to the version according to FIG. 5 or two adapter interfaces are provided for both variants.

FIG. 11 to FIG. 13*b* show perspective views of the clamping device 2. FIG. 13*a* shows the clamping device 2, which has the two clamping elements/clamping arms 4 and 4*a*. The clamping elements 4 and 4*a* are each arcuately shaped and gently taper at their respective free ends (bent outward), so that the clamping elements 4, 4*a* can be pulled off the tibia or ankle (resiliently) without injury and without the free clamping arm ends being able to scratch the patient’s skin.

Specifically, the clamping device 2 has a mounting block in the form of a T-piece 92 with a preferably cross-sectionally square (rectangular) insertion rod 93 and a hollow crossbeam 95, in which a spindle mechanism/spindle 90 is mounted, which can be rotated about its longitudinal axis by means of rotary knobs 304 arranged on the end face of the crossbeam 95. A carriage (tibia contact block) 86 is supported on the crossbeam 95, which is engaged by the spindle 90, so that the carriage 86 can be moved back and forth along the crossbeam 95 during manual rotation of the spindle 90 by means of the rotary knobs 304. The carriage 86 further comprises a central/central contact area 78 as well as two contact arms 82 aligned in a V-shape with respect to each other, at the free end portions of which a ratchet mechanism 76 is arranged/installed in each case, where one clamping element 4, 4*a* engages in each case in such a way that the clamping elements 4, 4*a* are pivotably mounted on the contact arms 82 and can be pivoted manually towards each other (in the closing direction), the respectively associated ratchet mechanism 76 initially preventing a pivoting back (in the opening direction).

Furthermore, each ratchet mechanism 76 has a biasing spring 77 (these are shown in particular in FIG. 11 as leg springs), which bias the associated clamping elements 4, 4*a* in the opening direction. Finally, each ratchet mechanism 76 has a ratchet lever 84 via which the associated ratchet mechanism 76 can be unlocked/released.

The clamping elements 4 and 4*a* are made of a pre-bent (leaf) spring steel and consist of several prongs or fingers 62 arranged next to each other and spaced apart in the manner of a fork 60 so that the prongs/fingers 62 of the clamping elements 4, 4*a* facing each other can engage into one another in an overlapping manner when they are swiveled in the closing direction, thus ensuring secure fixation to the tibia 3.

Figure 11:
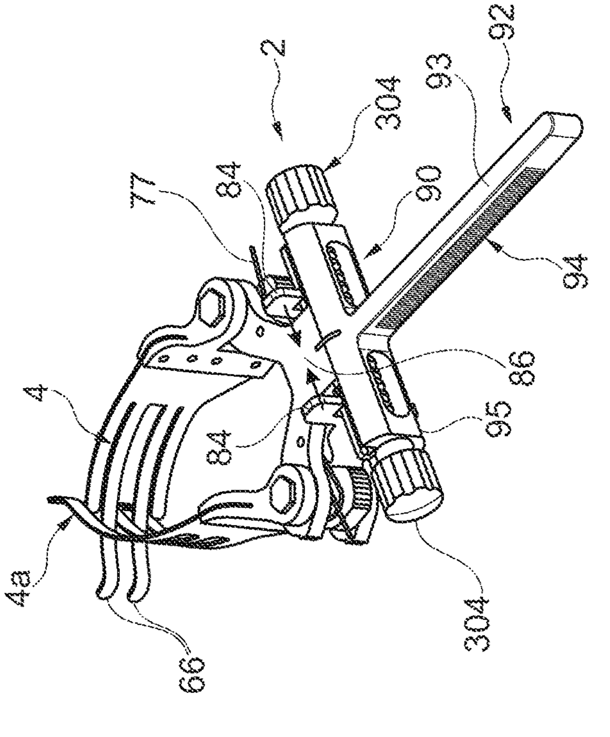
FIG. 11 shows a perspective view of the clamping device according to the invention with closed clamping elements.

FIG. 11 shows the clamping device 2 with the closed clamping elements 4 and 4*a*, which engage into one another in such a way that a tibia 3 can be sufficiently clamped or held thereon. To preload the clamping elements 4 and 4*a*, the ratchet levers 84 are first pressed in a movement directed away from each other, as a result of which latching pawls (these are shown schematically in FIG. 11 as pawls/teeth formed integrally with the ratchet levers 84) engage in an external toothing on the respective clamping elements 4, 4*a*. If the clamping elements 4, 4*a* are to be released, the ratchet levers 84 are pressed slightly inwards (towards each other) (see FIG. 11), which disengages the latching pawls from the associated clamping elements 4, 4*a* and thus eliminates the ratchet effect. Via the spindle mechanism 90, to which the rotary knobs 304 are attached, the clamping elements 4, 4*a* can be moved in both directions along the crossbeam 95 via the common carriage 86. The spindle mechanism 90 is integrated in the crossbeam 95, as already explained above. In this way, the clamping elements 4, 4*a* can be optimally aligned in the transverse direction of the tibia in the state already embracing the tibia, without exposing the patient or the physician to a risk of injury, e.g. as a result of protruding parts of the spindle, etc.

The T-piece 92, in cooperation with the carriage 86 and the contact arms 82 arranged thereon, forms a substantially Y-shaped tibia contact block assembly unit which can be inserted into a corresponding distal ankle shackle receptacle 5 on the side of the telescopic device 10.

For this purpose, the T-piece 92 forms the mandrel/insertion rod 93, which is preferably rectangular in cross-section and has a latching/gripping structure 94 on at least two longitudinal sides facing away from each other, by means of which the entire clamping device 2 or assembly unit is movably fastened or can be movably fastened to the telescopic device 10 or the receptacle 5 thereof.

Figure 12:
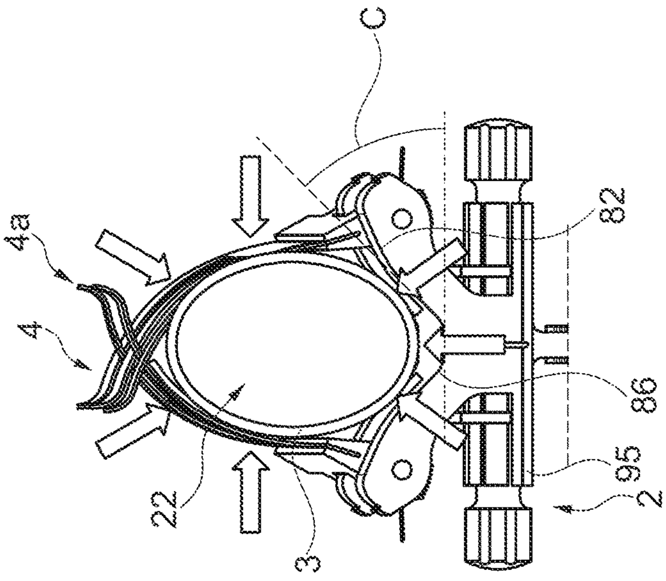
FIG. 12 shows a plan view of the clamping device according to the invention with closed clamping elements.

FIG. 12 shows the clamping device 2 in plan view and in the closed state, with the oval-shaped region 22 for receiving the tibia (shown schematically in FIG. 12) being formed between the clamping elements 4, 4*a*. Here, the tibia 3 is received by the V-shaped contact block/element 86 including the lateral contact arms 82 and the clamping elements 4, 4*a*. Between the V-shaped contact block 86 and the lateral contact arms 82, an angle C is formed in the central contact area 78, which amounts to preferably 45° on each side (i.e. the two contact arms 82 enclose a common angle of approx. 90°). Thus, a particularly ergonomic contact of the tibia is created in the V-shaped contact block 86.

Furthermore, FIG. 12 shows the directions of force application to the tibia 3 that are achievable with the ankle shackle 2 according to the invention.

Accordingly, the two clamping elements 4, 4*a* completely enclose the tibia in that their prongs/fingers intersect/get caught/overlap with each other at the posterior side of the tibia, thus pressing the tibia against the frontal contact block/carriage 86. Since the clamping elements 4, 4*a* are pre-bent and also resilient, they can at the same time also apply a clamping force to the tibia from the sides, effectively chucking it all around. This is clearly illustrated by the force arrows in FIG. 12.

Figure 13A:
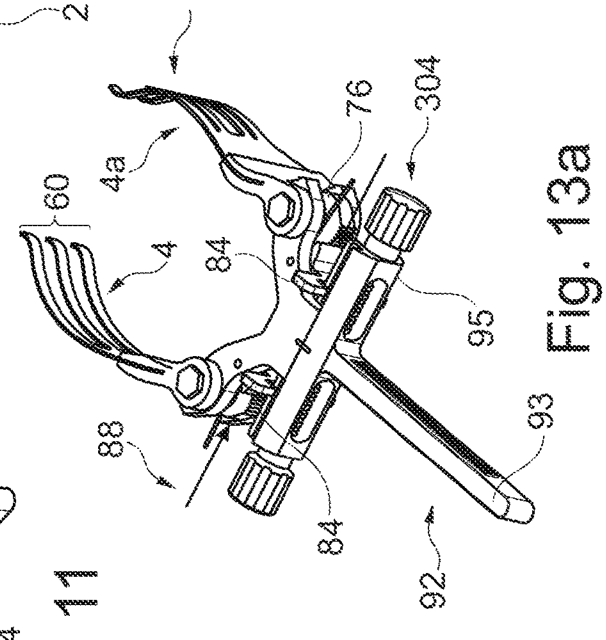
FIG. 13*a* shows a perspective view of the clamping device according to the invention with open clamping elements.

FIG. 13*a* shows the clamping device 2 with the clamping elements 4, 4*a* in the open position so that a tibia can be inserted. Moving the ratchet levers 84 towards each other releases the clamping elements 4, 4*a* or the ratchet mechanism, so that the clamping elements 4, 4*a* can be brought into an open position due to the internal spring bias, whereas moving the two ratchet levers 84 away from each other reactivates the ratchet mechanism so that the clamping elements 4, 4*a* can be individually brought into a closed position and latched in place there.

As already explained above, the rotary knob(s) 304 is/are provided to effect a lateral adjustability of the carriage/tibia contact block 86 and the clamping elements 4, 4*a* mounted thereon, and the spindle 90, which can be actuated by means of the rotary knobs 304 for displacing the carriage 86 is integrated into the T-piece 92 or the crossbeam 95.

Figure 13B:
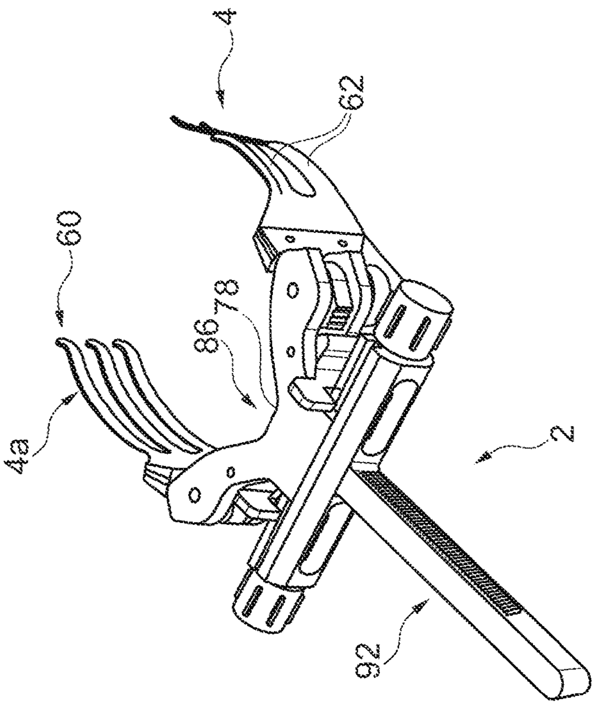
FIG. 13*b* shows a further perspective view of the clamping device according to the invention with open clamping elements.

FIG. 13*b* shows the clamping device 2 together with the respective clamping elements 4 and 4*a*, which in turn are designed to engage into each other through the respective forks 60, so that the tibia is clamped almost all around and, if necessary, an almost constant chucking force is effected in the circumferential direction.

Figure 14:
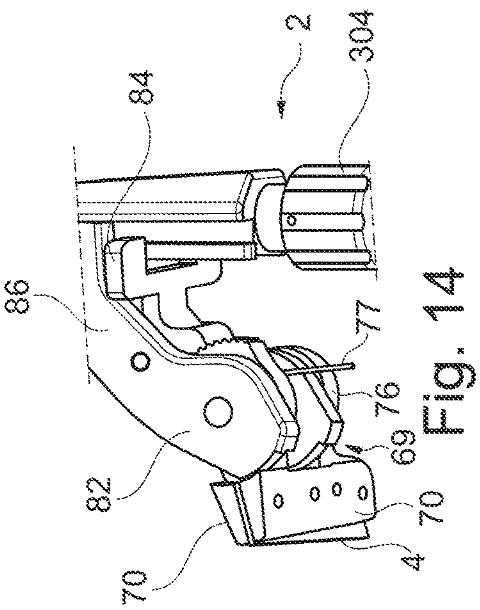
FIG. 14 shows a ratchet mechanism of the clamping device according to the invention of FIGS. 13*a* and 13*b,*

FIG. 14 shows the clamping device 2 and a hinge area 86 of a clamping element 4 and of the contact block/carriage 86. The clamping element 4 is coupled to the ratchet mechanism 76, which can be released via the ratchet lever 84, while only one ratchet lever 84 is shown in FIG. 14. The latching pawl (without reference sign) of the ratchet lever 84 can be seen, which engages in an external toothing in the hinge area of the clamping element 4 in a spring-loaded manner, as well as the ratchet lever 84 integrally connected thereto for disengaging the latching pawl from the external toothing. Further, the rotary knob 304 is illustrated, by means of which the tibia contact block 86 is adjustable/movable in the lateral direction.

Figure 15:
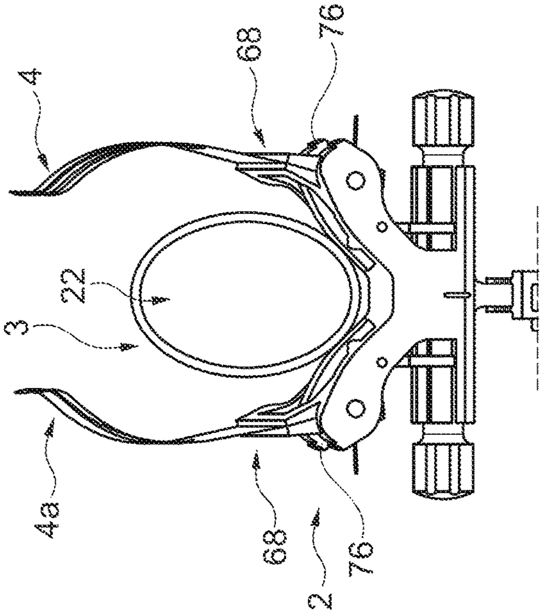
FIG. 15 shows the clamping device according to the invention of FIGS. 13*a* and 13*b* with inserted tibia and with open clamping elements.

FIG. 15 shows a top view of the clamping device 2 in the open state. The clamping elements 4, 4*a* are coupled to the ratchet mechanism 76 via their respective (inner/close-to-hinge) ends/hinge areas 68. The clamping elements 4, 4*a* are preferably made of thin sheet metal or other elastic material. At their free ends/tips 66, the clamping elements 4, 4*a* each point (radially) outward (are bent outward) to allow injury-free removal or withdrawal of the respective clamping elements 4, 4*a* from the tibia. The ends 68 of the clamping elements 4, 4*a* close to the hinge are preferably reinforced with a plastic part (reinforcing element) 70 (or sheathed with plastics), in particular to bring about a gentle introduction of moments into the further structure in such a way that the clamping elements 4, 4*a* are sufficiently fatigue-resistant.

Figure 16:
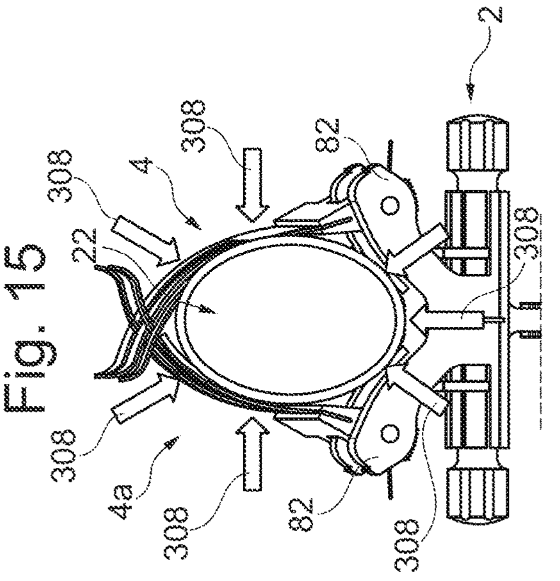
FIG. 16 shows the clamping device according to the invention of FIGS. 13*a* and 13*b* with inserted Tibia and with closed clamping elements.

FIG. 16 also shows the clamping elements 4, 4*a* in the closed state. Between the clamping elements 4, 4*a*, the oval-shaped region 22 for receiving the tibia or ankle is formed. The clamping elements 4, 4*a*, the V-shaped contact element/contact block/carriage 86 and the respective lateral contact areas/contact arms 82 of the contact block 86 create the force effect 308 acting circumferentially around the tibia. Specifically, the clamping elements 4, 4*a* are designed such that the force effect 308 acts on the tibia at several different locations in the circumferential direction of the tibia so that the tibia is firmly held all around.

From FIG. 13*b* in conjunction with, for example, FIG. 3, the spatial arrangement of the clamping arms 4, 4*a* with respect to the contact block 86 or the T-piece 92 can be seen.

Consequently, the clamping arms 4, 4*a* (in the manner of a shovel) are arranged offset in height with respect to the T-piece 92, i.e. they do not lie in the same plane as the T-piece 92. This has the direct consequence that in the case of a rotary position according to FIG. 3, the clamping arms 4, 4*a* are located below the T-piece, whereas in the case that the T-piece 92 is rotated by 180°, the clamping arms 4, 4*a* come to lie above the T-piece 92.

At this point, it should be recalled that the insertion mandrel 93 according to FIG. 13*a* is a square profile and the receptacle 5 at the distal end of the telescopic device 10 consequently forms a rectangular reception duct into which the insertion mandrel 93 is inserted and latched in place therein. This means that depending on the direction of rotation of the T-piece 92, the distance between the clamping arms 4, 4*a* (above or below the T-piece 92) and the proximally arranged saw block 8 is increased or decreased, as a result of which the overall length spectrum of the telescopic device 10 can be additionally reduced or increased on the whole.

Figure 17A:
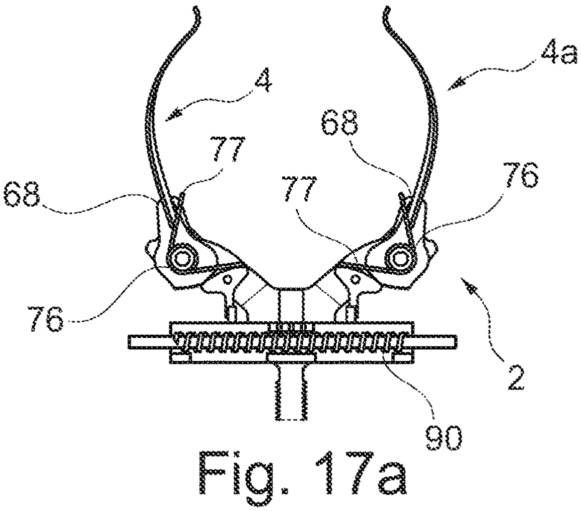
FIGS. 17*a*, 17*b*, 18 and 19 show the ratchet mechanisms of the clamping device in various adjustments.
Figure 17B:
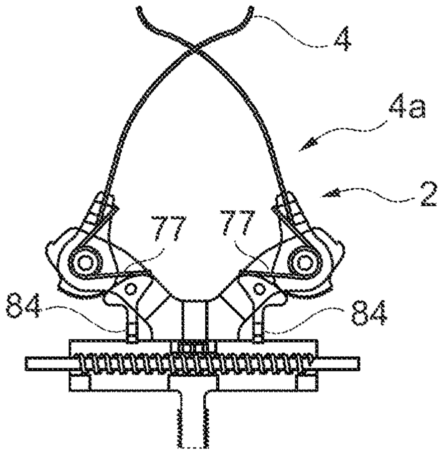

FIGS. 17*a*, 17*b*, 18 and 19 each show the clamping device 2 in cross-section. FIG. 17*a, b* show the clamping elements 4, 4*a*, which are coupled in each case to the ratchet mechanism 76 via the close-to-hinge ends 68 of the clamping elements 4, 4*a*. FIG. 17*a* shows the open clamping position and FIG. 17*b* shows the clamping elements 4, 4*a* in the closed clamping position. The springs 77, which preload the clamping elements 4, 4*a* in the opening direction, and the two ratchet mechanisms 76 with adjoining ratchet levers 84 for manual, individual disabling of the ratchet action can be seen.

Figure 18:
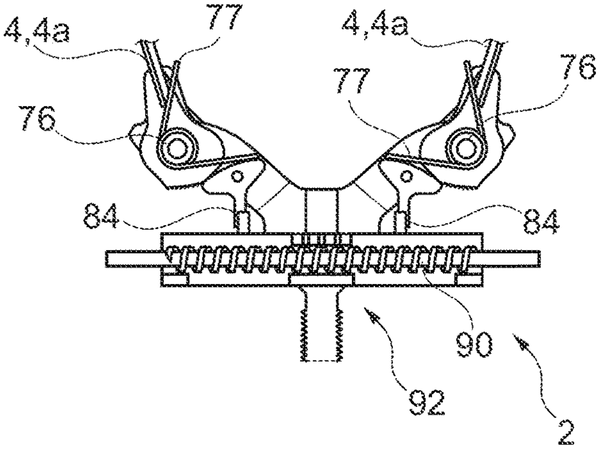
Figure 19:
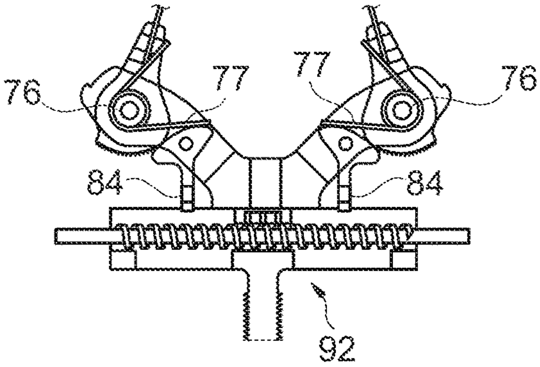

FIGS. 18 and 19 show an enlarged view of the clamping device 2 with the respective clamping elements 4, 4*a*, which are coupled to the respective ratchet mechanism 76. In addition, the relaxed return spring 77 of the respective ratchet mechanism 76 can be seen in each case.

The clamping device 2, which is also referred to as a foot clamp, is designed such that the telescopic device 10 can be pulled off both at the proximal adapter interface 12 of the tibia saw block 8 and, in a particularly simple handling action, from the patient's tibia in a way that is gentle on the tissue (i.e. atraumatic), for which purpose the spring elasticity of the clamping arms 4, 4*a* is exploited. This means that in case a surgeon wants to remove the telescopic device 10 from the tibia while leaving the saw block 8 on the tibia, he or she only has to press the pushbutton 16 to uncouple the saw block 8 from the telescopic device 10 and at the same time simply pull off the clamping device 2 (without actuating the ratchet lever 84).

Furthermore, the spring elasticity of the clamping arms 4, 4*a* results in an almost constant clamping force over the circumference of the tibia, so that hematomas due to punctual application of force can be avoided. The clamping device 2, i.e. the foot clamp, is particularly distinguished for this object by the fact that the clamping elements 4, 4*a*, i.e. the retaining elements of the ankle shackle 2, are sufficiently elastic so that they can be easily pulled off the distal tibia without operating a release mechanism, and that at the same time they have a sufficiently high rotational and translational stability against unintentional adjustment of the ETA, and that the ratchet mechanism 76 can also be opened manually by means of the ratchet levers 84.

The ratchet mechanism 76 is made operative/inoperative via the respective ratchet lever 84. Furthermore, it is possible not to simply pull the clamping elements 4, 4*a* off the tibia, but to release the ratchet lever 84. The two clamping elements 4, 4*a* are then automatically opened by the return spring 77 after actuation of the ratchet levers 84 and thus release the tibia.

As already explained above, the adapter interface for the tibia saw block 8, i.e. for the tool guiding device, is designed in such a way that the saw block adapter 12 forming the adapter interface can be actuated by simply pressing the pushbutton 16 with the thumb to release the telescopic device 10 from the saw block 8, as a result of which a retaining mechanism 18 (described in more detail below) releases the saw block 8. Due to the variants described above with regard to the saw block 8 as well as the clamping device 2, it is now possible, after fastening the saw block 8 to the tibia and operating the saw block adapter 12 (i.e. actuating the retaining mechanism 18), to pull the telescopic device 10 including adapter 12 and clamping device 2 off the patient's tibia with one (single) hand and a thumb pressure as well as by utilizing the spring elasticity of the clamping arms 4, 4*a*, without any further operating action being necessary. This facilitates the handling of the entire alignment device 1 to a considerable extent.

Figure 20:
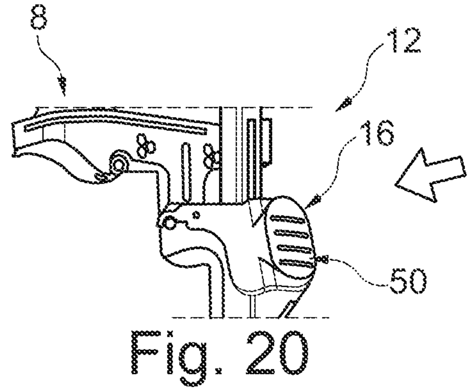
FIGS. 20-23 show the decoupling device according to the invention in combination with the tool guiding device in various positions.

FIG. 20 to FIG. 23 show different perspective views of the tool guiding device/saw block 8 in combination with the decoupling device/saw block adapter 12. In FIG. 20, the tool guiding device 8 is (selectively) attached to/coupled in the decoupling device 12. The decoupling device 12 has the retaining mechanism 18 including the pressure element 16, which preferably has a relief-like surface 50. The thumb pressure force of the respective treating physician presses on the relief-like surface 50 of the pressure element 16.

Figure 21:
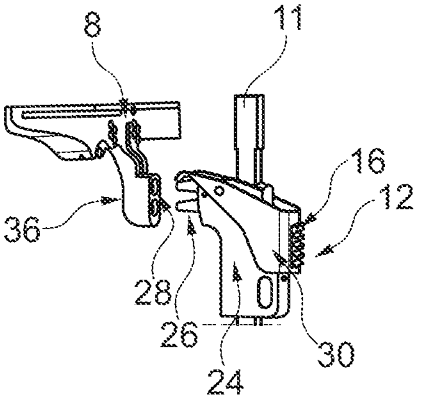

FIG. 21 shows the interaction of the tool guiding device 8 with the decoupling device 12. Specifically, the tool guiding device 8 has an adapter socket 36, which in turn has a plurality of female receiving elements 28. It is preferred that each of the female receiving elements 28 is a recess/bore in the adapter socket 36, which are provided to positively receive the respective male receiving elements/protrusions/pins 26 of the decoupling device 12. The fitting of the respective male receiving elements 26 in the respective female receiving elements 28 ensures a secure support of the tool guiding device 8 on the decoupling device 12 in all three spatial directions. The decoupling device 12 also mounts the retaining mechanism 18 in the form of a retaining bracket or hook element 30, which is provided to enclose the adapter socket 36 of the tool guiding device 8 and to get caught in/on it at a corresponding undercut 44.

Figure 22:
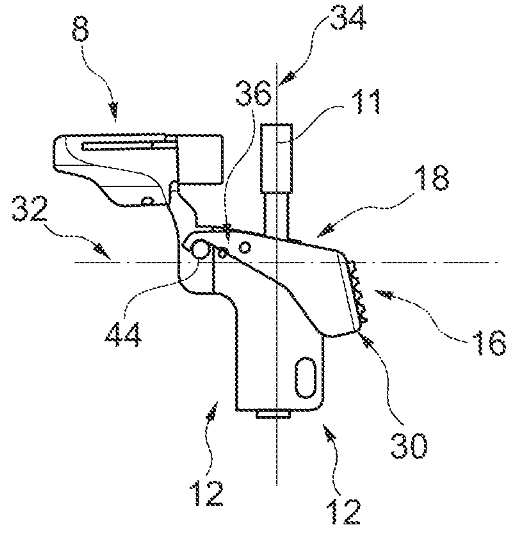

FIG. 22 shows a side view of the tool guiding device 8 and the saw block adapter 12 in the coupled state. Accordingly, the securing bracket 30 preferably consists of a sheet metal component which is bent so as to form a substantially U-shaped hollow profile, the two, respectively free-ending webs/side flanks of the U-profile, being formed into hooks and the connecting web of the U-profile being formed into the pressure element 16. This securing bracket 30 formed in this way is hinged to a base body 24 of the saw block adapter 12 on both sides thereof (i.e. the base body 24 is received in the hollow U-profile). The hollow U-profile thus forms a kind of rocker with the pressure element 16 on one side and the hooks on the other side of the rocker hinge. In the coupled state according to FIG. 22, the hooks of the securing bracket 30 engage with the undercuts 44 in the form of bolt- or pin-like protrusions on the saw block 8, in particular on its mounting/adapter socket 36, and thus retain it on the adapter interface of the saw block adapter 12.

In addition, FIG. 22 indicates a lateral actuation button on the base body 24 of the saw block adapter 12, which interacts with a latching mechanism (symbolically shown on the lower end face of the saw block adapter 12), by means of which the saw block adapter 12 can be coupled to the handle 14 at the upper end face thereof (upper handle section) in order to selectively form a unit with the handle 14, as shown for example in FIG. 15.

Figure 23:
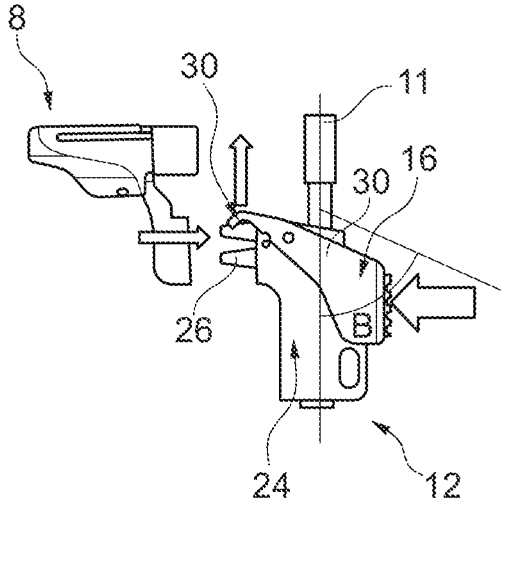

FIG. 23 shows the mode of operation of the decoupling device/saw block adapter 12 (in particular of the retaining mechanism) and of the tool guiding device/saw block 8, which is to be coupled to the base body 24 of the decoupling device 12.

It can be seen that by actuating the pressure element 16 by thumb pressure, the securing bracket 30 can be pivoted, while its hooks can be lifted. In this state, the saw block 8 can be placed onto the adapter interface of the decoupling device 12, while the male protrusions/pegs 26 are inserted into the female recesses/holes 28 according to the plug-and-socket principle. Finally, the pressure element 16 is released, whereupon the hooks of the securing bracket 30 (by gravity or spring-loaded) swing downward, engaging behind the protrusions 44 on the saw block 8 (see FIG. 22). The decoupling device 12 is separated from the saw block 8 in the corresponding reverse manner.

Figure 24:
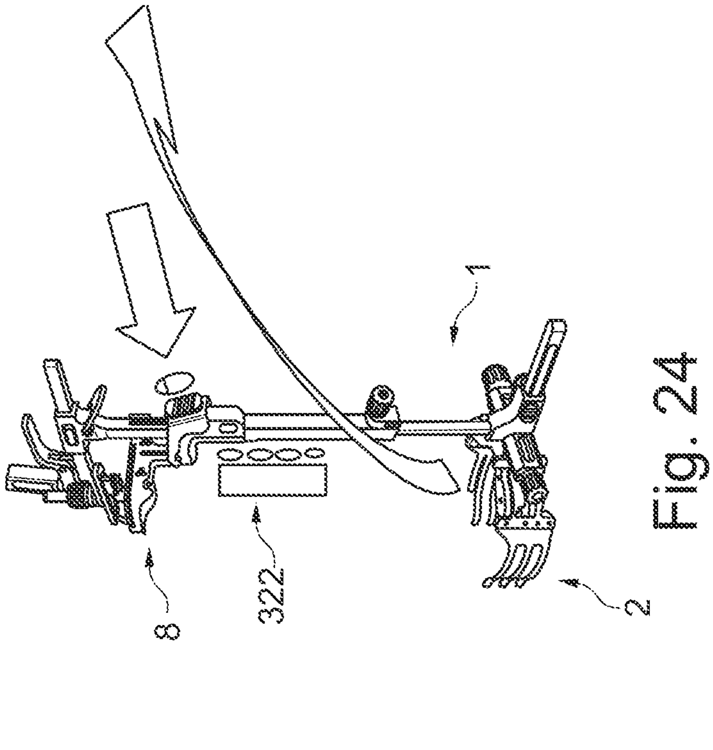
FIG. 24 shows the draw-off direction of the alignment device according to the invention.

FIG. 24 shows the removal direction of the alignment device 1 (the telescopic device 10 together with the foot clamp 2 and adapter 12) when the tool guiding device 8 is/remains attached to the tibia and is thus to be separated from the telescopic device 10. The treating physician presses with the force of his thumb on the relief-like surface 50 of the pressure element 16 (as a result of which the retaining bracket 30 releases the saw block 8) and simply pulls the telescopic device 10 together with the clamping device 2 off the patient's tibia. In so doing, the clamping device 2 is not opened separately, but the clamping elements 4, 4*a* are spread open (automatically) due to their spring elasticity during removal. The indicated hand 322 of the treating physician encloses here the telescopic device 10 or the handle 14.

Figure 25:
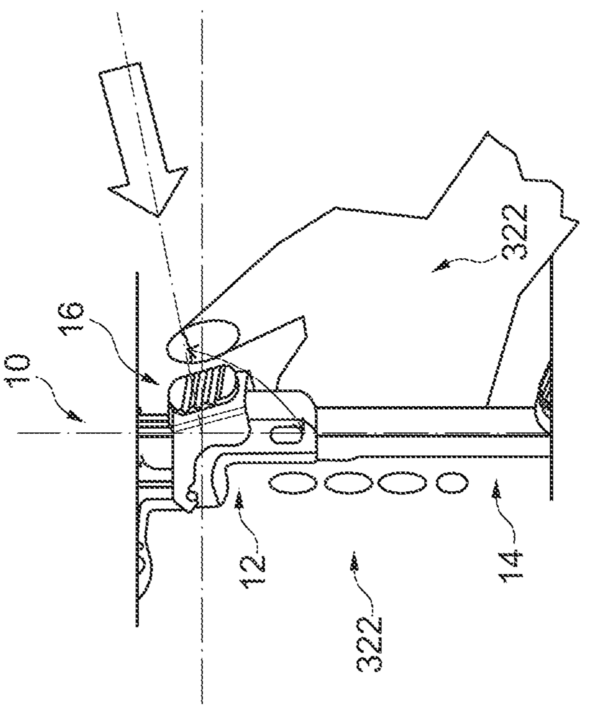
FIG. 25 shows a perspective view of the decoupling device according to the invention.

FIG. 25 shows the hand 322 of the treating physician, which effects the thumb pressure force on the pressure element 16 of the telescopic device 10. The fingers of the hand 322 of the treating physician embrace the telescopic device 10 at the handle 14.

Figure 26:
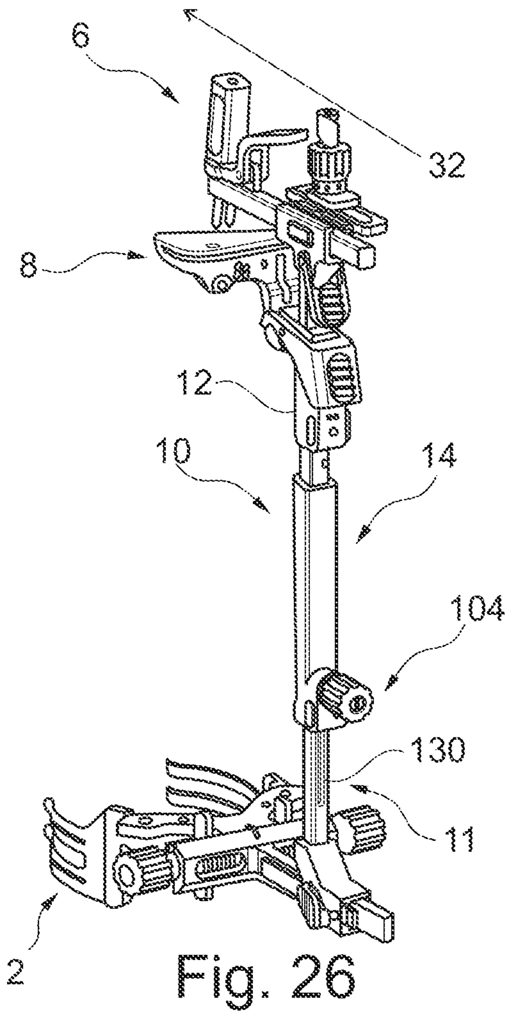
FIG. 26 shows a further perspective view of the alignment device according to the invention.
Figure 27:
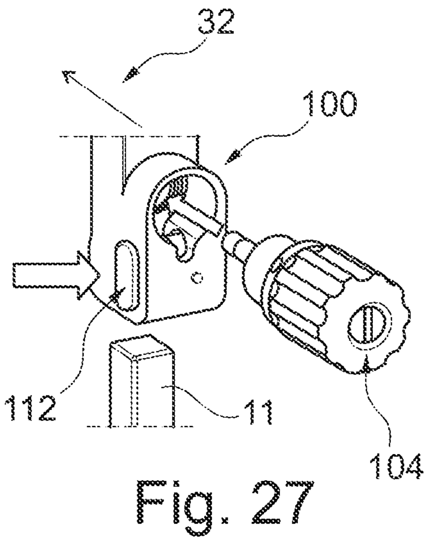
FIG. 27 shows a first perspective view of the securing element according to the invention.

FIGS. 26 and 27 show the alignment device 1 according to the present invention with the telescopic device 10 according to a "proximal fixation variant", wherein in the distal region of the telescopic device 10 again the clamping device 2 preferably according to the above description is provided and in the proximal region again the tool guiding device 8 preferably according to the above description is arranged via the adapter 12, to which preferably the contact device 6 is attached/attachable. The transverse direction 32 indicated in FIGS. 26 and 27 means a direction of approach to the tibia of a patient.

An arresting or securing element 104 is provided on the telescopic device 10 (in all fixation variants), which can preferably be inserted into the telescopic device 10 upstream of the alignment device 1 as seen in this transverse direction 32. The securing element 104 is provided, among other things, to secure the telescopic device 10 in various positions in a self-locking manner in a selected length position and/or to allow it to be pulled apart freely. The securing element 104 is further provided to be inserted in the transverse direction 32 into a receiving element/receiving portion 100 formed on the handle 14. Further, a locking element 112 is arranged on the receiving portion 100, which is designed to be manually moved into a release position in which the securing element 104 is removable from the receiving portion 100, whereas the locking element 112 holds the securing element 104 in the receiving portion 100 in an (unactuated) latching position.

Figure 28:
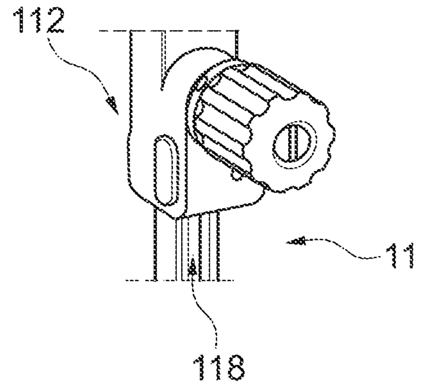
FIG. 28 shows a further perspective view of the securing element according to the invention.

FIG. 28 shows the slide rod element 11 in an enlarged view, according to which, on a side facing the securing element 104, a longitudinal groove-shaped recess (hereinafter referred to as longitudinal groove) 118 is formed on the slide rod element 11, which is distally and proximally limited by an end stop defining the minimum and maximum extension position (telescopic stroke) when the securing element 104 is in sliding engagement with the longitudinal groove 118.

FIG. 29 to FIG. 35 show various detail views of the securing element 104.

Figure 29:
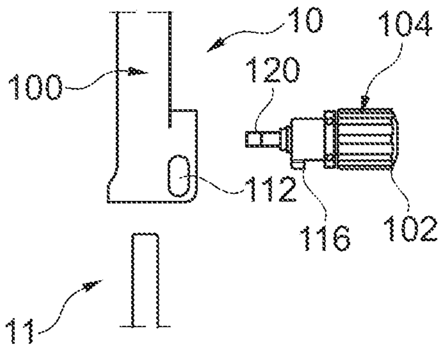
FIGS. 29-35 show various detail views of the securing element according to the invention.

FIG. 29 shows the securing element 104 in side view, which is provided to be inserted into the corresponding receiving portion 100 on the telescopic device 10 and retained therein by means of the locking element 112. The corresponding receiving portion 100 is provided at the distal end portion of the handle element 14. The handle element 14 encloses the slide rod element 11. Also clearly visible in FIG. 29 is a peg 116 projecting radially (downward) from the securing element 104, which is used as an engagement element/undercut for the locking element 112. Other latching engagement solutions are of course also conceivable, such as a bayonet lock or a screw connection, etc.

Figure 30:
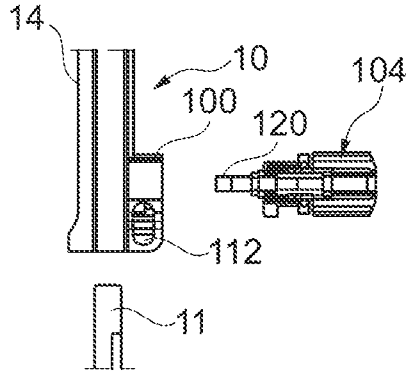

FIG. 30 shows the receiving portion 100 together with the locking element 112 and the securing element 104 in a partial cross-section. Accordingly, the securing element 104 generally consists of a spring-biased inner bolt 120, which is axially movably supported in a rotary knob 102 to engage into the longitudinal groove 118 of the slide rod element 11, and of a preferably sleeve-shaped housing 114 for rotatably receiving the rotary knob 102 for applying an arresting force to the slide rod element 11 while bypassing the spring bias or in parallel with the spring bias.

Figure 31:
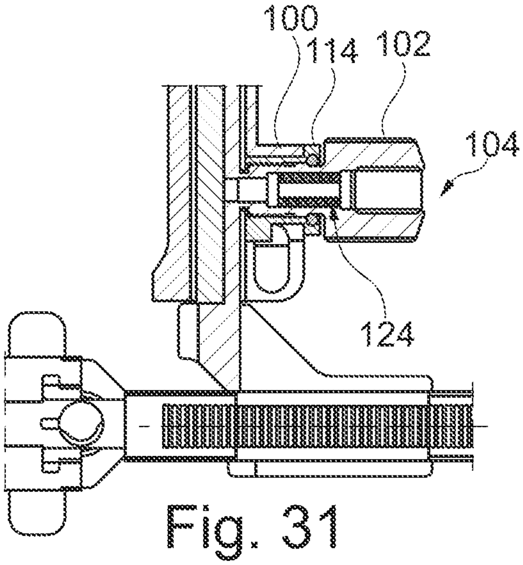
Figure 32:
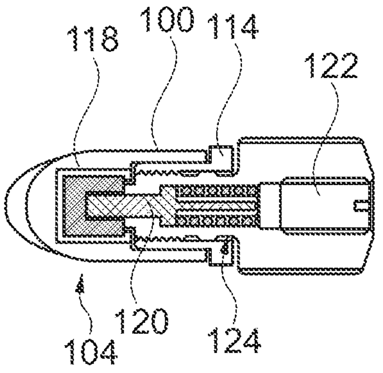
Figure 35:
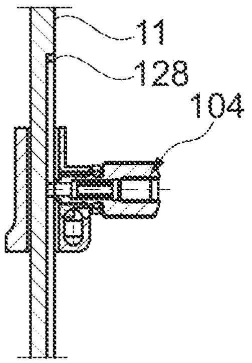

FIGS. 31 and 32 show the locking element 104 in detail, which is inserted into the receiving portion 100 of the handle 14. Accordingly, a slide block (without reference sign) is received in the longitudinal groove 118 of the slide rod 11, in/on which the bolt 120 is axially supported. The bolt 120 has/forms a spring plate in its central portion, on which in turn a helical spring 124 is supported in order to apply a pretensioning force to the bolt 120 in the direction towards the slide block. The spring plate is simultaneously used as a stop element that strikes against a shoulder in the rotary knob 102, preventing the bolt 120 and the spring 124 from falling out of the rotary knob 102. The bolt 120 as well as the biasing spring 124 are received in the rotary knob 102 in its axial direction, which is axially inserted/screwed into the preferably sleeve-shaped housing 114, which in turn is inserted into the receiving portion 100 and held/secured therein by means of the locking element 112 (see in particular FIG. 31). A set screw 122 is screwed into the rotary knob 102 at the end face (at its free end face), which is used as an abutment for the biasing spring 124. Accordingly, if the set screw 122 is turned within the rotary knob 102, the spring bias on the bolt 120 (within the rotary knob) can be changed in this manner.

In addition, the bolt 120 has a coil portion 121 that extends from the spring plate toward the set screw 122 and is surrounded by the biasing spring 124, thus guiding the biasing spring 124.

Figure 33:
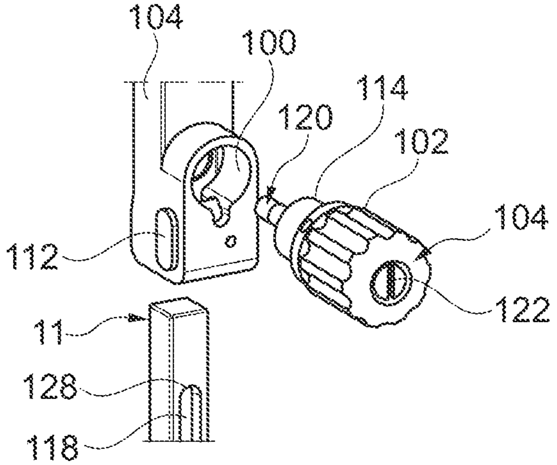
Figure 34:
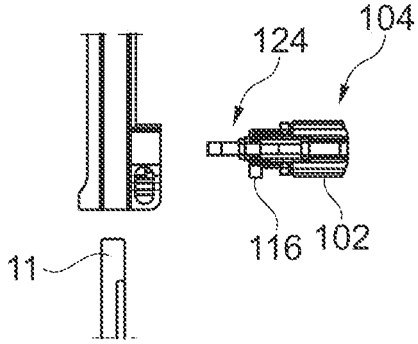

FIG. 33 shows the securing element 104 with its adjusting element/set screw 122, e.g. its adjusting screw, which is provided for adjusting the pretensioning forces acting on the bolt (clamping pin) 120. Furthermore, the locking element 112 can be seen, which effects the locking of the securing element 104 in the receiving portion 100 of the handle 14. In the lower area of FIG. 33, the slide rod element 11 is shown, which shows the (upper) stop portion 128 of the groove-shaped recess 118, which represents one of the two maximum extension positions 128, 130 of the slide rod element 11 with respect to the handle 14.

The mode of operation of the securing element 104 is briefly explained below with reference to FIGS. 31 to 35:

First, the securing element 104 is inserted into the receiving portion 100 (into a bore formed therein), preferably in a sliding manner, and its sleeve-shaped housing 114 is secured in a rotationally and axially fixed manner by means of the locking element 112. In this state, the bolt/clamping pin 120 within the rotary knob 104 projects into the longitudinal groove 118 of the slide rod element 11 and applies a compressive force thereto (indirectly via the slide block received in the longitudinal groove 118) as a function of the preload force of the spring 124. In this manner, the preload force of the spring 124 can be increased and/or decreased by turning the set screw 122 within the rotary knob 104 to thereby change the frictional force between the slide rod 11 and the bolt 120 of the securing element 104. This allows, for example, to reduce the friction to virtually zero or to increase it such that at least any displacement of the current stroke position of the telescopic device 10 due to gravity is avoided.

In order to fix (freeze) the stroke position, the rotary knob 104 can be further screwed into the sleeve-shaped housing 114, as a result of which the rotary knob 104, as from a certain screw-in position in the housing 114, presses directly, i.e. in concrete terms via the coil portion 121 of the bolt 120 (which is now axially supported on the set screw 122 in the rotary knob 102) on the slide block and presses/braces the latter directly against the slide rod 11 while bypassing the spring bias.

In the following, the height sensing device (also referred to as a height arresting or height adjustment unit) 6 is described with reference to FIGS. 36 to 44.

Figure 36:
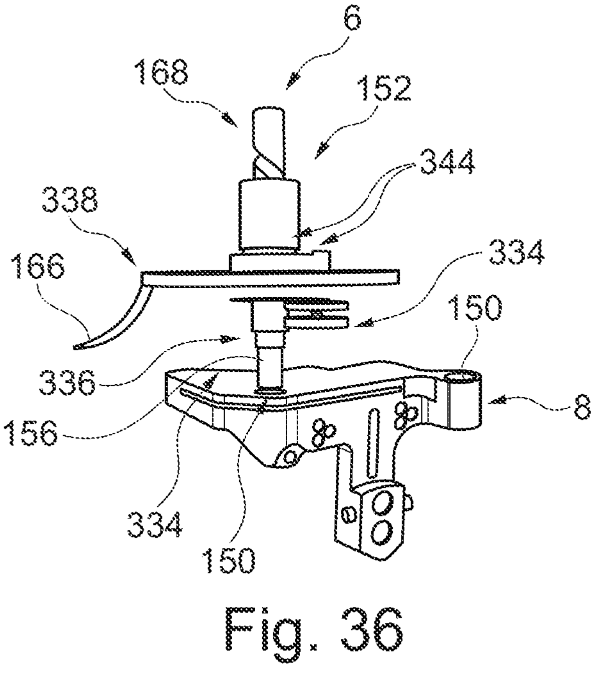
FIG. 36 shows a perspective view of the contact device according to the invention.

FIG. 36 shows the tool guiding device/saw block 8 preferably as described above, which comprises/has a seating recess/bore 150 into which the height sensing element/height adjustment unit 6 can be selectively inserted. In this context, the tool guiding device 8 has only one or more seating bore(s)/seating recess(es) 150, while it is to be noted at this point that a side notch with a clamping strap, a magnetic holder or the like can also be provided instead. The at least one seating recess 150 forms part of an adapter interface 334 between the tool guiding device/saw block 8 and the height adjustment unit 6.

In principle, the height adjustment unit 6 essentially consists of

- a contact tip 166 mounted or formed on a contact arm 338 (together forming a height sensing assembly 152),
- a spindle mechanism 168, on which the contact arm 338 is supported for at least one height adjustment, and
- an insertion mandrel/shaft 156 preferably with a latching device/latching mechanism 154 as a further part of the adapter interface 334 for coming into engagement with the seating recess 150 from a top side 151 of the saw block 8.

Figure 37:
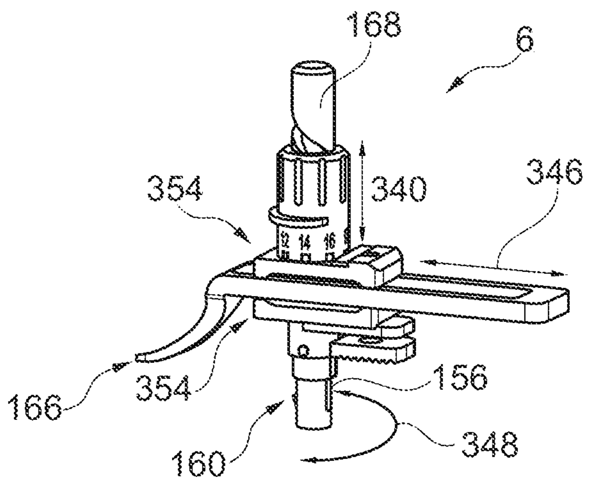
FIG. 37 shows a further perspective view of the contact device according to the invention.

FIG. 37 shows a perspective view of the height adjustment unit 6 according to the present invention. Accordingly, the height adjustment unit 6 has a horizontal movability degree of freedom 346, a vertical adjustment degree of freedom 340 and a rotational degree of freedom 348. For this purpose, the height adjustment unit 6 has the insertion mandrel/shaft 156, which is preferably designed as a hollow shaft and can thus accommodate the latching device 154 therein, which can be brought into undercutting operative engagement with the seating recess 150 on the side of the saw block 8 for axially fixing the height adjustment unit 6 on the saw block 8. For this purpose, a spring-biased detent nose 160 is provided in the insertion mandrel 156, which protrudes laterally/radially beyond the circumference of the shaft 156 and can be retracted into the insertion mandrel 156 by means of an actuating button 158 in order to release a detent engagement with the saw block 8. The rotational degree of freedom 348 is thus effected by the rotational freedom of the insertion mandrel/shaft 156 in the receiving bore 150 of the tibia saw block 8.

The contact arm 338 is provided with an elongated hole (see FIG. 37), which is penetrated by the spindle mechanism/spindle 168 (sliding/free), to which the contact arm 338 is coupled via an interposed frictional element/holding carriage 354, which holds the contact arm 338 under friction but longitudinally movably (in extendable manner) on the spindle mechanism 168. The horizontal movability degree of freedom 346 is thus caused by the horizontal movability of the height sensing assembly 152 or contact arm 338 on the spindle mechanism 168 (via the frictional element 354).

Figure 38:
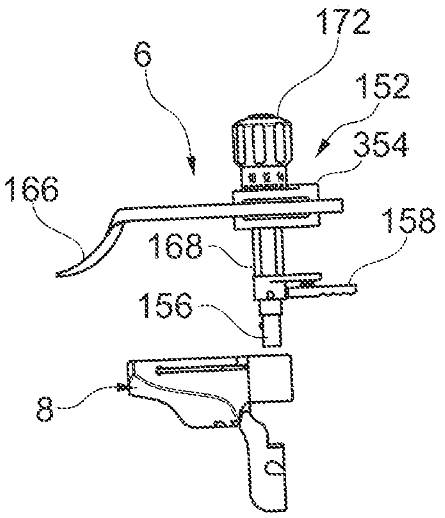
FIG. 38 and FIG. 39 show further perspective views of the contact device according to the invention.

FIG. 38 shows the height sensing element 6 in side view, which is provided to be inserted into the tool guiding device 8. Accordingly, the height sensing element 6 has, on its lower side (facing the saw block 8), the insertion mandrel 156 and the actuating element in the form of a lever 158 which, in the unactuated state, bears against a lever stop (without reference sign) arranged or formed on the insertion mandrel 156. Further, to contact the bony landmark of the tibia, the contact tip 166 is provided at the outer (proximal) end of the contact arm 338. Finally, the spindle mechanism is shown with a spindle/spiral 168 axially coupled to the insertion mandrel 156 and carrying the frictional element 354 including the contact arm 338 in its central portion.

Figure 39:
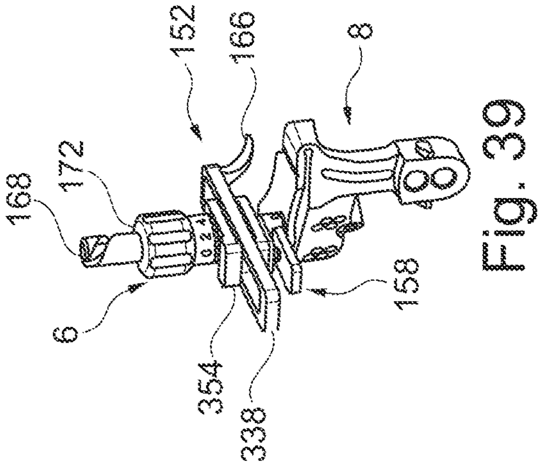
Figure 40:
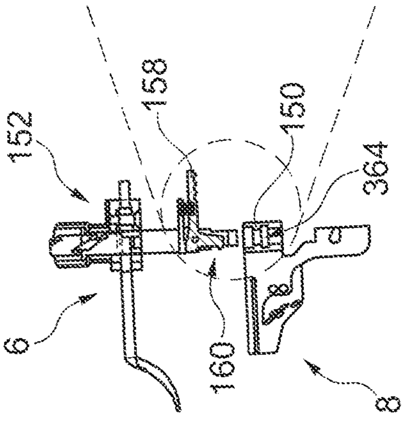

FIGS. 39 and 40 show a perspective view of the saw block/tool guiding device 8, in which the height adjustment unit 6 is already inserted. The spindle mechanism of the height adjustment unit 6 has the spindle/spiral element 168 already indicated above as well as a spiral wheel 172, which is provided/mounted on the spiral element 168. The spiral wheel 172 is coupled in a relatively rotatable manner with the frictional element 354, so that the latter (including the contact arm 338) is held (axially movable) on the spindle 168 via the spiral wheel 172.

Figure 41:
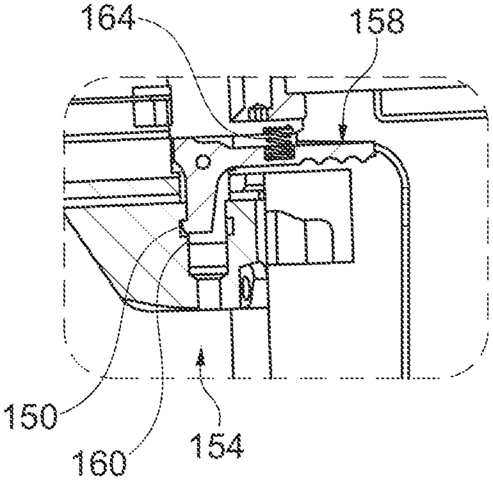
FIG. 40 and FIG. 41 show detail views of the contact device according to the invention.

A detail of FIG. 40 is shown in FIG. 41. FIG. 41 shows the detent device 154 with the detent nose 160, which is inserted into the seating recess 150 on the saw block 8. Furthermore, a spring element 164 can be seen which is arranged between the lever stop and the actuating lever 158 for actuating the detent nose 160 and biases the lever 158 into a position in which the detent nose 160 is in a detent engagement position (radially protruding according to FIG. 41). Specifically, the lever 158 is designed as a two-legged right-angled deflection lever pivotally mounted in its central portion within the insertion mandrel 156, with one leg forming the actuation lever/actuating portion and the other leg being operatively connected to the detent nose 160, which is preferably designed in the form of a push block and is urged radially outward by the one leg of the actuation lever 158 via its spring bias.

Figure 42:
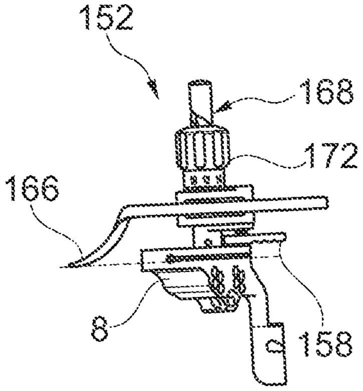
FIGS. 42-44 show further perspective views of the contact device according to the invention.
Figure 43:
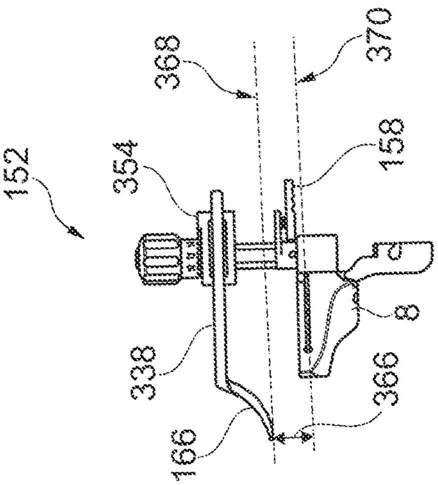
Figure 44:
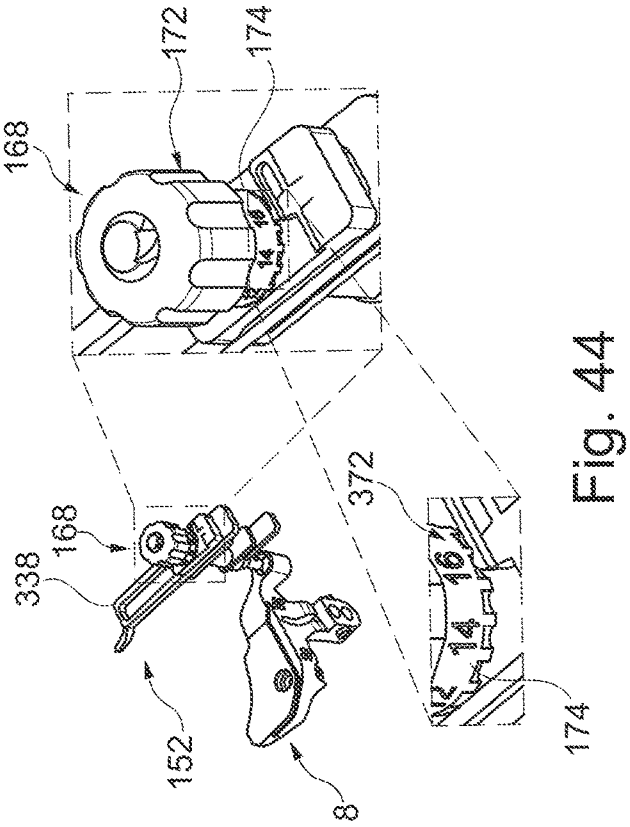

FIG. 42 and FIG. 43 show the tool guiding device/saw block 8 with the inserted height adjustment unit 6 in different adjustment positions.

Between the adjustment position according to FIG. 42 and the adjustment position according to FIG. 43, the adjusted cutting height/cutting height difference (also referred to as contact level) 366 can be seen. The contact level 368 defines the height of the contact tip 166 relative to the horizontal saw slot in the saw block 8, which defines the cut level 370.

FIG. 44 again shows the tool guiding device 8 with the attached height sensing element 152, which includes the spiral element/spindle 168. In turn, the spiral element 168 is operable via the spiral wheel 172 to adjust the height of the height sensing assembly 152. Specifically, the spiral/spindle 168 is guided for relative rotation preferably in the insertion mandrel 156, with the height sensing assembly 152 being threadedly mounted on the spiral element 168 via the frictional element 354. The spiral wheel 172 is in turn (as a further component of the height sensing assembly 152) mounted for relative rotation on the frictional element 354, so that rotation of the spiral wheel 172 on the spiral/spindle 168 results in a displacement of the contact arm 338 along the spindle 168. Finally, a latching mechanism 372 is preferably arranged between the frictional element 354 and the spiral wheel 172, which is provided to maintain a defined height (axial position on the spindle) of the height adjustment element 152.

The mode of operation of the height adjustment unit/cutting height feeler 6 according to the present invention can be summarized as follows:

The adjustable cutting height feeler 6 has the basic function of being provided as a simple assembly and disassembly unit on the tool guiding device 8, i.e. on the tibia saw block. Attached to the distal end of the stylus, i.e., the height arresting unit 6, is the spring-loaded latching mechanism, which is denoted here throughout by reference sign 154. The latching mechanism 154 arrests the stylus after the latter has been put/inserted into the seating recess (through hole) 150 of the tibia saw block 8 provided for this purpose, while the stylus preferably remains rotatable about the insertion axis.

The axial arresting is achieved via the spring-loaded detent nose 160. This means that during putting/inserting the insertion mandrel 156 into the seating recess 150, the spring-loaded detent nose 160 is pushed laterally back into the insertion mandrel 156 due to its outer beveled (distal) contact/sliding surface, and when fully inserted in the tibia saw block 8, the detent nose 160 is preferably latched in place in a groove in the tibia saw block 8. From the latching position, the spring-loaded detent nose 160 is released by means of the actuation lever 158, which retracts the detent nose 160 against the spring 164 when the actuation lever 158 is manually pivoted. In this state, the stylus can be easily removed from the saw block 8. The contact tip 166 further causes a bony landmark of the tibia to be sensed. The landmark selected by the user is the reference relative to which the cutting height of the tool guiding device 8 is adjusted by rotating the spiral wheel 172 accordingly. The landmark is detected by the contact tip 166, which is attached to the end of the contact arm 338. Due to the tactile accuracy of the contact tip 166, even very small bony structures can be detected visually very well and accurately by means of eye control.

The horizontal movability of the height sensing assembly 152, in particular of the contact arm 338 is used for adaptation to the different anatomies of the tibia and to achieve the medial and lateral tibial alignment from the same adapter location. For this purpose, the horizontal movability of the contact arm 338 at the frictional element 354 is provided, which is shown in FIG. 37. With the help of the rotating stylus and the contact arm 338, which can be moved along its main axis, any bony landmark on the proximal surface of the tibia can be reached. The dimensions of the contact arm 338 are designed in such a way that the anatomy existing worldwide (e.g. of Asian or Caucasian people) can be taken into account.

In order to maintain the desired extended length of the contact arm 338, the contact arm 338 is secured in self-locking manner on the frictional element 354 by means of frictional engagement against displacement in axial direction. Due to the fact that the stylus latches in place in the tool guiding device 8, i.e. in the tibia saw block, and a defined stop of the stylus on the saw block 8, the distance of the contact tip 166 of the stylus relative to the lower edge of the saw key in the saw block 8 is safely achieved, the set cutting height being indicated, for example, by numbers 344 on the circumference of the spiral wheel 172. The number indicating the set height is preferably indexed with a pointing element at the anterior end of the frictional element 354 (holding unit).

For example, setting the tibia section thickness from 0 to 16 mm (or from 0 to 14 mm) is achieved with only one rotation of the spiral wheel 172. A stop element/stop portion at the upper end of the spiral 168 prevents the spiral wheel 172 from being completely unscrewed from the stylus.

After setting the desired cutting height relative to the contact tip 166, the height sensing assembly 152 is moved against the landmark selected by the user and the alignment device is aligned. The landmark is approached in particular by (manually) moving the handle 14 with the mounting elements along the slide rod 11 with the distal clamping device 2 being already in engagement. Once the alignment device 1 is aligned with regard to height, varus, valgus and slope as desired by the user, the tool guiding device 8, i.e. the saw block, is finally firmly anchored to the bone with fixation pins, preferably nails, through the fixation holes 300 provided for this purpose. Afterwards, the stylus must/can be removed in order to be able to perform the tibial saw cut. For this purpose, the telescopic device 1 can remain on the tibia or simply be removed together with the clamping device 2 and the adapter 12, whereas the saw block 8 (without the already removed contact device 6) remains on the tibia.

In the following, a proximal fixation unit/fixation device 202 is described, which can selectively be mounted on the proximal end portion of the telescopic device 10 preferably as described above, in order to convert an alignment device of the anterior fixation version into an alignment device of the proximal fixation version.

Figure 45:
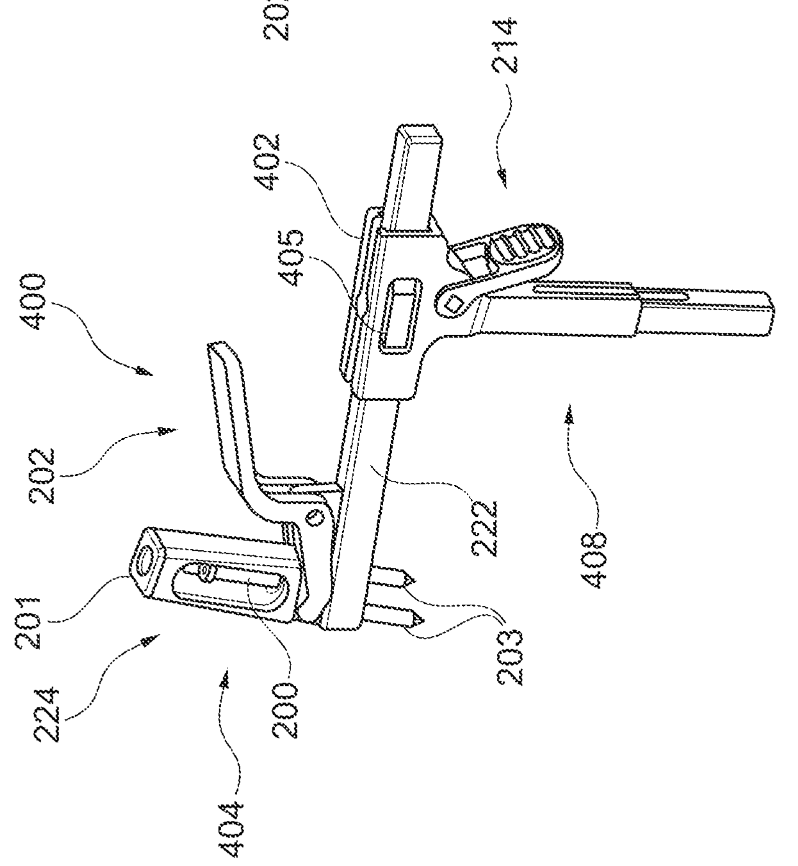
FIG. 45 shows a first perspective view of the drive device according to the invention.
Figure 52:
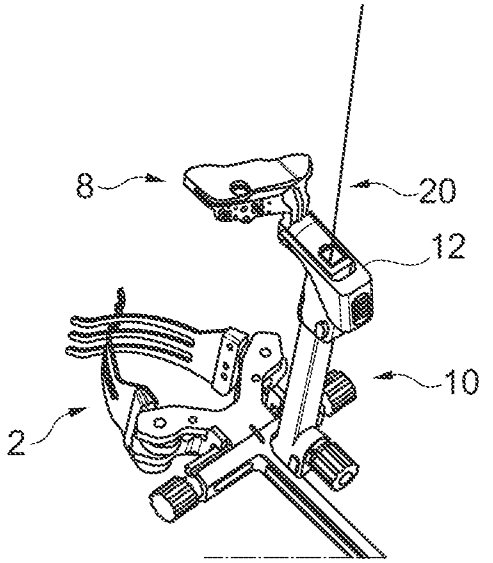
FIGS. 52-55 show perspective views of the alignment device according to the invention.

For this purpose, FIG. 45 shows an optional proximal drive device/fixation unit 202, preferably comprising at least the following:

- a drive mechanism 224 designed to drive in preferably two pins slidably guided in the drive mechanism 224,
- an impact lever 400 provided and designed for releasing the two pins driven in, and
- a connecting mechanism 406 for a (preferably clamping) connection between the proximal fixation unit 202 to the alignment device (telescopic device) according to the version "anterior fixation" for selectively/temporarily creating an alignment device in the version "proximal fixation".

Specifically, the fixation device 202 has a transverse beam 222 at one free end portion of which the drive mechanism 224 and the impact lever 400 are disposed. The drive mechanism 224 has a drive pin unit 404, which is used as a kind of anvil for the preferably two drive pins. For this purpose, a central guide pin 200 is (fixedly) anchored in the transverse beam 222 at an angle close to 90° relative to the transverse beam's longitudinal axis, on which the anvil is slidably mounted in the form of a frame/frame housing 201 surrounding the guide pin 200. On an underside of the anvil/frame 201 facing the transverse beam 222, the preferably two drive pins 203 are fixed in parallel alignment to the guide pin 200, which are preferably mounted/guided in two through holes on the transverse beam 222. If a hammer blow is thus manually applied to the anvil, the pins 203, which are held/fixed thereto and guided longitudinally in the transverse beam 222, are driven into a patient bone, with the impact direction being ensured by the guide pin 200 which is fixed to the transverse beam 222 and guides the anvil longitudinally.

The impact lever 400 is hinged to the transverse beam 222 in a rocker-like manner and has an engagement portion on a side facing the drive mechanism 224, which is in operative engagement with the anvil/frame housing 201, and an impact portion on an opposite side, which can be struck with a hammer or similar impact tool. That is, when the impact portion of the rocker-like impact lever 400 is struck, its engaging portion exerts a force on the underside of the frame housing 201 in opposition to the pin impact device, thereby pulling the pins 203 out of the patient bone.

The transverse beam 222 is axially slidably inserted in an accommodation case/fixation element 402, which accommodates a slip/sliding brake (indicated in FIG. 45) 405, for example in the form of a curved leaf spring, that slows down an axial sliding movement of the transverse beam 222 in the accommodation case 402. In this context, the transverse beam 222 is preferably made of a polygonal profile (rectangular profile) so that rotation of the transverse beam 222 about its longitudinal axis in the case 402 can be prevented.

Fixed to the accommodation case 402 is a support column 408 which is aligned at a substantially right angle or slightly inclined to the transverse beam 222 and in/on which the connecting mechanism 406 is preferably provided in the form of a latching/clamping mechanism 208 (see in particular FIG. 47) for selectively fastening the fixation unit 202 to the telescopic device 10. According to FIG. 47, this clamping mechanism 208 consists essentially of a wedge-shaped clamping plate 216 that rests against the free distal end face of the support column 408, the end face of the support column 408 being preferably beveled/inclined in a wedge shape with respect to the longitudinal axis of the column. The support column 408 is formed from an at least partially tubular (hollow) body 210, in which a tension element (tension rod) or control element 210 is mounted in longitudinally movable manner. The clamping plate 216 is operatively connected via the tension element (tension rod) or control element 210 guided in the support column 408 to an actuating lever 214, which is pivotably mounted on the accommodation case 402 for the transverse beam 222. According to FIGS. 48 and 49, the actuating lever 214 has an actuation portion with a preferably roughened or ribbed pushbutton for a nonslip pressurization of the actuating lever 214, for example by means of a thumb of the user. Consequently, if the actuating lever 214 is flipped and hence a tensile force applied to the tension rod 210, the wedge-shaped clamping plate 216 is thereby displaced radially outwards along the (wedge-shaped) chamfered end face 218 of the support column 408, thereby artificially increasing the overall cross-sectional area of the column 408.

The support column 408 also has a region with a small cross-section (cross-sectional area) at its (distal) end portion facing away from the case and a region with a large cross-section (cross-sectional area) in its (proximal) end portion facing the case, which are separated from each other by a circumferential shoulder (see in particular FIG. 48). The region with small cross-section is dimensioned such that it can be inserted (with slight play) into the hollow telescopic rod/slide rod element 11 of the telescopic device 10 and arrested therein by means of the clamping mechanism 208. The region of large cross-section corresponds substantially to the outer cross-section of the slide rod element 11, so that when the support column 408 is fully inserted in the slide rod element 11 (up to the circumferential shoulder as a stop), a substantially smooth slide rod surface is produced.

Figure 46:
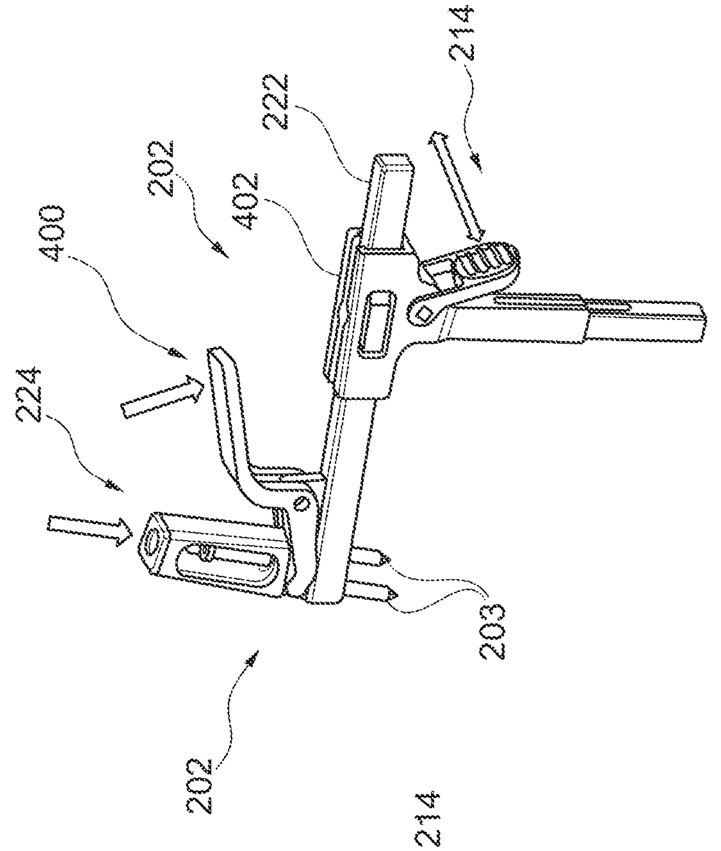
FIG. 46 shows a further perspective view of the drive device according to the invention.

FIG. 46 shows the fixation unit 202 with the drive mechanism 224 including their actuation options. Fixation is thus effected by driving in the pins 203 preferably by a hammer blow. A further hammer blow against the impact lever 400 releases the pins 203. The clamping mechanism 208 is activated/deactivated by actuating the pushbutton 214.

FIG. 47 shows the fixation unit 202, which comprises the fixation mechanism 224 and the connection/clamping mechanism 208. If the connection/clamping mechanism 208 or its manual actuation lever 214 is in the upwardly pulled position (toward proximal), the clamping action between the support column 408 and the slide rod element 11, into which the support column 408 is inserted in the proximal fixation variant of the alignment device 1, is cancelled. Here, the connection/clamping mechanism 208 acts via the control element/pull rod 210 on the wedge-shaped clamping plate 216, which is movable radially outwards or inwards with respect to the support column 408 by the chamfer 218 of the distal end face of the support column 408. As soon as the clamping plate 216 is pulled upwards (toward proximal) via the pull rod 210 by pushing the actuating lever 214 downwards (toward distal), the clamping plate 216 is moved laterally, in particular radially outwards into a clamping position with the slide rod 11, into which the support column 408 is already inserted. If, on the other hand, the lever 214 is pressed upwards, the control element 210, i.e. the rod, moves downwards (toward distal) and releases the clamping plate 216. The latter moves radially inwards as a result of its wedge shape, which removes the clamping effect.

FIG. 47 shows an enlarged view of the closed clamping mechanism 208 according to FIG. 48, in which the actuating lever 216 has been moved downward, as already described above. Accordingly, the wedge-shaped clamping plate 216 is also beveled at its side facing the support column 408 at an angle of approximately 45° with respect to the central axis of the plate. An approximately equal bevel is also found on the free (distal) end face of the support column 408, so that in the event of an operative/sliding engagement of both bevel sides, the clamping plate 216 remains aligned approximately perpendicular to the central axis of the support column 408. However, as an alternative to this design, it is also possible according to FIGS. 48 to 51 to provide a type of expanding cone at the distal end/end portion of the hollow support column 408 that pulls the distal end portion into the hollow/tubular support column 408 and elastically expands it radially if the actuating lever 214 is actuated accordingly. For this purpose, the support column 408 may be formed with expanding slots (not further shown) in its distal end portion. It is also conceivable to provide an elastic bracing body (e.g., made of a plastic material) at the distal end of the support column 408, which is axially compressed when the lever 214 is actuated, thereby displacing plastic material radially outward.

FIGS. 52 to 55 show the alignment device in the "anterior fixation variant", in particular its telescopic device 10 comprising the tool guiding device 8 already adapted to the telescopic device 10. A longitudinal axis 20 extends in the longitudinal direction of the telescopic device 10 as a reference axis, which also represents the central axis of the slide rod 11 according to FIG. 52 at the same time. The saw block adapter 12 is clearly visible, which is guided (along the longitudinal axis 20) so as to be axially movable over the slide rod 11 by means of the adapter above/proximal to the handle 14, with the slide rod 11 protruding at the top side (proximal side) of the saw block adapter 12 from the through opening formed therein and accommodating the slide rod 11, as shown for example in FIG. 54.

Figure 53:
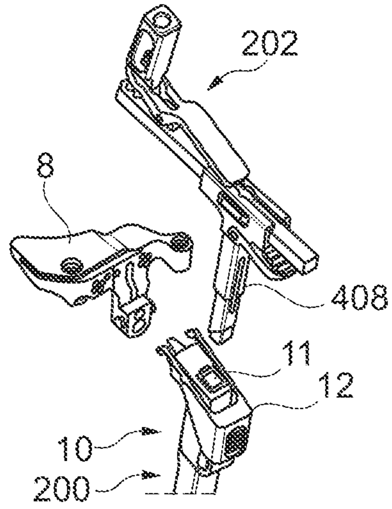

FIG. 53 shows the telescopic device 10 in exploded view, according to which the slide rod 11 is designed as a hollow shaft that has an open end face toward proximal. The illustrated exploded view shows the tool guiding device/saw block 8 and the optional fixation unit 202 for selectively establishing the alignment device 1 as a "proximal fixation variant". The outer dimensions of the slide rod 11 as well as of the support column 408 of the fixation unit 202 are clearly illustrated, in such a way that the support column 408 can be inserted in its distal end portion with a small outer diameter almost without play into the slide rod 11 not more than up to the shoulder for a length adjustment/adaptation of the slide rod 11 to the patient's anatomy, which separates the support column's own distal end portion with small outer diameter from the proximal portion with large outer diameter, which essentially corresponds to the outer diameter of the slide rod 11.

Figure 54:
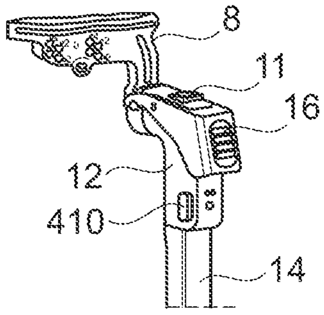
Figure 55:
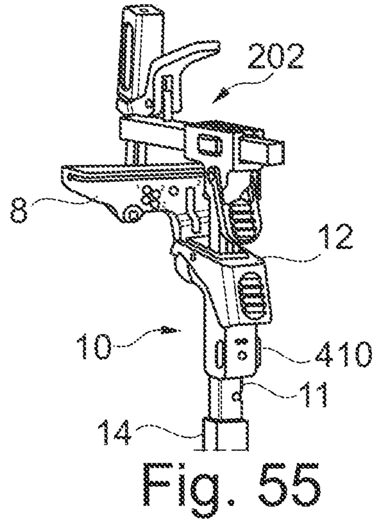

FIG. 54 shows the tool guiding device 8 and the adapter 12 placed on the slide rod 11 above the handle 14, the actuating element of which, preferably the push/pushbutton 410, being not actuated/depressed so that the tibia cut block adapter 12 is arrested on the handle 14 of the telescopic device 10 to form a unit. In this state, the handle 14 can be shifted relative to the slide rod 11 for alignment of the contact needle 166. This corresponds to an alignment device 1 of the anterior fixation variant. In contrast, FIG. 55 shows the telescopic device 10 in which the pushbutton 410 on the adapter 12 has been pressed and thus the tibia cut block adapter 12 is released from the handle 14 and thus freely movable relative to it. The drive device 202 is inserted into the hollow body/slide rod element 11. This corresponds to the alignment device 1 in the proximal fixation variant, according to which the telescopic device 10, i.e. the slide rod 11, is extended by the support column 408 toward proximal, thus forming an extended movement guide for the saw block adapter 12.

Figure 56:
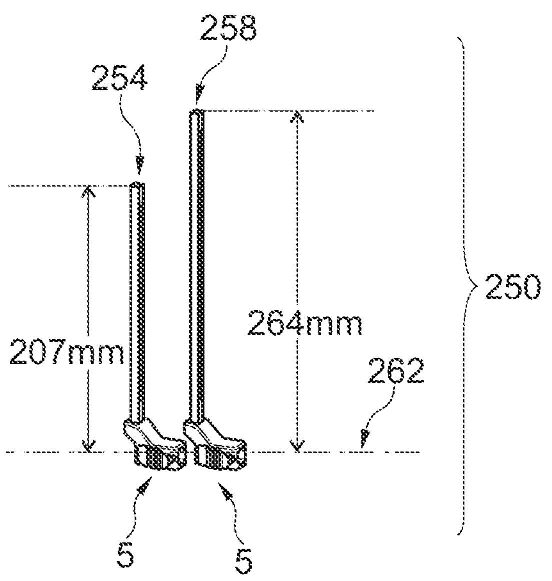
FIG. 56 shows the slide rods in different lengths.

FIG. 56 shows at set 250 of slide rod elements, for example comprising at least two slide rod elements 254 and 258 of differing lengths. By way of example, the first slide rod element 254 has a first (short) length, which is for example 207 mm, which thus characterizes the short slide rod. The second slide rod 258 has a second (long) length that is different from the first length and is, for example, 264 mm. The longitudinal axis of the foot clamp reception device/reception duct 5 defines the respective lower point of the slide rods 254, 258, from which the slide rod length can be measured in each case.

It should be noted at this point that the set 250 of slide rods according to the invention can also have more than two slide rods of differing lengths. As an alternative or in addition to this, it is also perfectly conceivable to provide several fixation units with support columns 408 of differing lengths in one set for this purpose, in order to take different patient anatomies into account.

Figure 57:
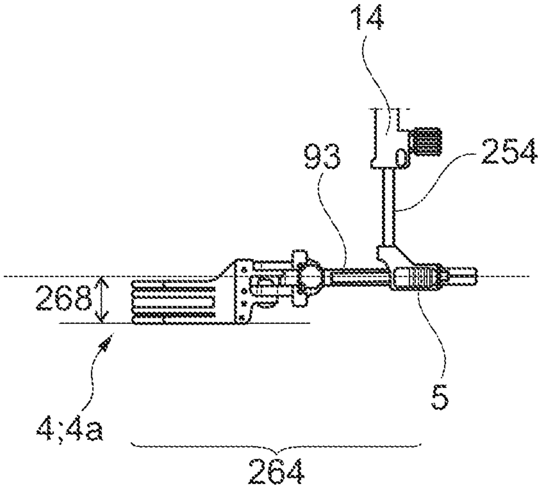
FIG. 57 and FIG. 58 show the clamping device according to the invention.

FIG. 57 shows the distal end region of the telescopic device 10 with the foot clamp reception device/reception duct 5, which is attached to the first (short) slide rod 254. The cantilever arm 93 is received here by the foot clamp reception device 5. The clamping elements 4, **4*a* are arranged to be offset with respect to the cantilever arm 93 by a corresponding rotational orientation of the cantilever arm 93 in the reception duct 5** towards the distal end. This results in a change in length of +15 mm compared to a central clamping element arrangement, as already explained above.

Figure 58:
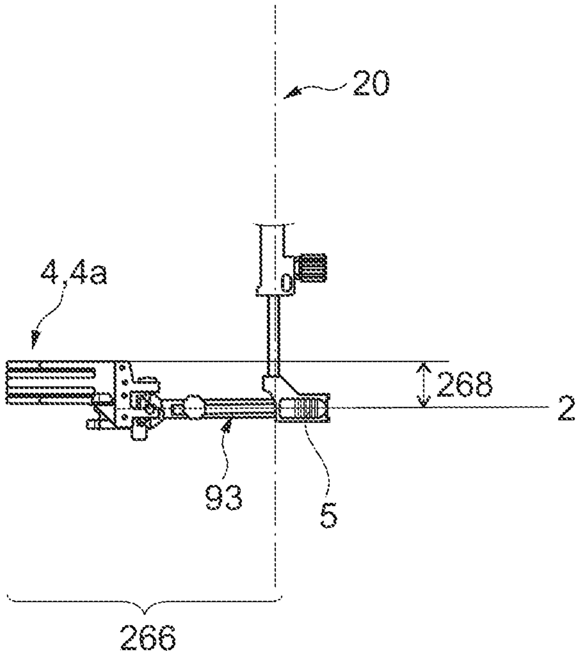

FIG. 58 shows a second position of the foot clamp device. In this case, the clamping elements 4, **4*a* are offset towards the proximal end (i.e. upwards) with respect to the cantilever arm 93, as a result of which the cantilever arm 93 is in turn accommodated by the foot clamp reception device 5. The central axis of the foot clamp reception devices 2 and the upper edge of the foot clamp elements 4, 4*a* show the height offset 268**. In the second position, an average change in length of −15 mm is provided compared to a central clamping element arrangement.

Figure 59:
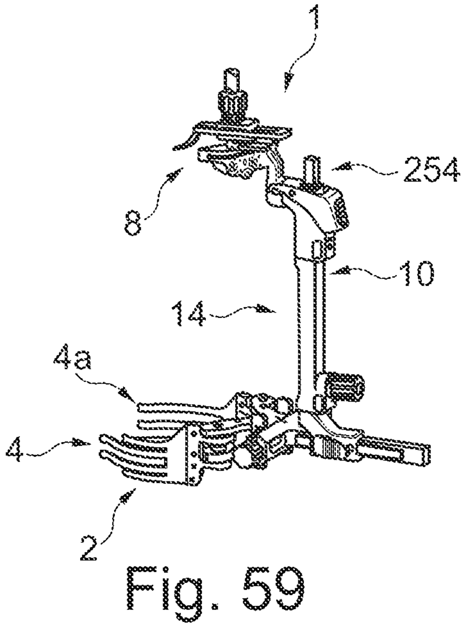
FIGS. 59-62 show further perspective views of the alignment device according to the invention.
Figure 60:
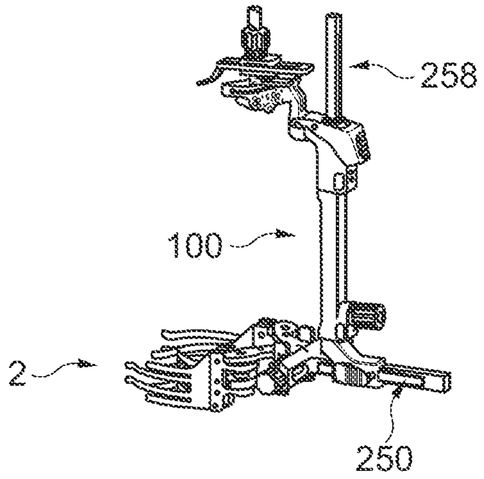

FIG. 59 shows the alignment device 1 with the tool guiding device 8, which is placed on the short slide rod 254. FIG. 60 shows the alignment device 1 with the long slide rod 258, which protrudes significantly further beyond the handle 14 toward proximal than the short slide rod version.

Figure 62:
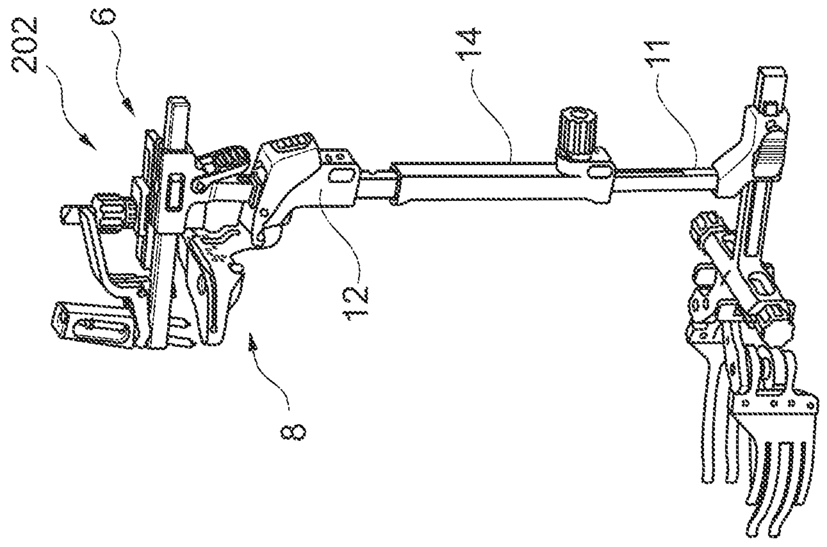
Figure 61:
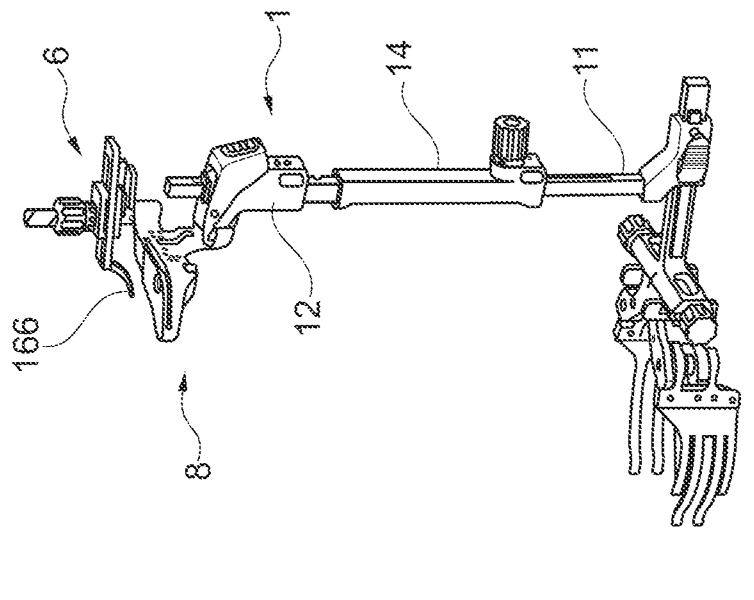

FIG. 61 shows the alignment device 1 with the tool guiding device 8 and the contact device 6 for the version "anterior fixation", in which the saw block adapter 12 is detached from the handle 14 for fine adjustment of the height distance between the contact needle 166 and the saw block 8. FIG. 62 shows the alignment device 1, which comprises the tool guiding device 8 and on which the contact device 6 with the drive device 202 for proximal fixation is additionally placed. Also in this case, the saw block adapter 12 is detached from the handle 14. By forming the set of slide rods of different lengths according to the invention, the alignment device 1 is applicable for the different leg lengths given worldwide, e.g. for Asians with short leg lengths or Caucasians with very long leg lengths. This is advantageously achieved by simply exchanging the slide rods with different rod lengths.

These length versions allow the following leg lengths to be adjusted:

The short slide rod 254 allows to adjust leg lengths of approx. 200 mm to approx. 380 mm, and The long slide rod 258 allows to adjust leg lengths from approx. 260 mm to approx. 438 mm.

Due to the overlap of the useful lengths of the two slide rod lengths 254 and 258 of about 120 mm, the user can opt for one of the slide rods 254, 258 and advantageously apply the alignment device 1 to a majority of patients.

With respect to the two embodiments for alignment, the length settings preferably differentiate as follows:

For example, for the "anterior fixation" shown in FIG. 61, the first slide rod 254 has a length 256 from about 200 mm to about 360 mm and the second slide rod element 258 has a length from about 260 mm to about 420 mm.

For the alignment device 1 of the embodiment "proximal fixation" shown in FIG. 62, the first slide rod 254 of the short slide rod length has a first length from 255 mm to about 380 mm. With respect to the second length of the second slide rod element 258, the second slide rod element, for the embodiment of proximal fixation shown in FIG. 62, has a length from about 315 mm to about 438 mm.

Furthermore, a change in length of + or −15 mm is achieved by the ability of turning the foot clamp 2 by 180°, as shown in FIGS. 57 and 58 according to the above description. This change in length is advantageously achieved without the need to replace the slide rod 11. The described change in length of + or −15 mm, which is achieved by the ability of turning the foot clamp, is already included in the above description of the change in length of the alignment device. For very short lengths of the tibia, it is still possible to reduce the adjustment to approx. 180 mm with the "anterior fixation", as shown in FIG. 61. However, this has the consequence that the oblong hole or drive slot 302 in the tool guiding device 8, i.e. in the tibia saw block, cannot be used for the primary anterior fixation version of the alignment device (the ETA).

Preferred embodiments of the alignment device 1 according to the invention are summarized below:

A first embodiment of the alignment device 1 for a tibial resection guide comprises:

a clamping device 2 having at least two clamping elements 4, **4*a* acting against one another for clamping the distal end of a tibia 3** of a patient;

a tool guiding device or saw block 8 for guiding a tool during the resection of the tibia 3, optionally, a contact device 6 for contacting the proximal end of the tibia 3, mountable to the tool guiding device 8; and a telescopic device 10 which is proximally connected to the tool guiding device 8 and distally connected to the clamping device 2 in separable manner and designed to align the devices 2, 6 with respect to the tibia 3, wherein the telescopic device 10 additionally comprises in its proximal region 52 a decoupling device or cut block adapter 12 designed to separate the saw block 8 from the telescopic device 10 upon manual activation; and/or that the clamping elements 4 of the clamping device 2 are flexurally elastic so that the telescopic device 10 can be removed from the tibia preferably after activation of the decoupling device 12 by utilizing the flexural elasticity of the clamping elements.

Further, it may be provided that the telescopic device 10 has a handle 14 in its proximal region 52, which handle is designed in such a way that it can be grasped by the one hand of an operator, and that the decoupling device/saw block adapter 12, above the handle 14, has an actuation/pressure element 16 for activation/saw block release, which is preferably arranged at an angle A 18 between 90° and 150°, more preferably at an angle A between 95° and 120° degrees and in particular at an angle A 18 of 100° to the longitudinal axis 20 of the telescopic device 10, so that the pressure element 16 can be actuated by the thumb of the one hand 56.

It may further be provided that the clamping device 2 is arranged in the distal region 54 of the telescopic device and that the two resilient clamping elements 4, 4*a* each have an arcuate shape which are aligned with respect to each other such that, when viewed in the direction of the longitudinal axis 20 of the telescopic device 10, they form between them, in the closed state, an oval-shaped region 22 which is provided for receiving the distal region of the tibia 3 in a clamping manner.

Further, it may be provided that the decoupling device 12 has a base body 24 comprising at least one male (or female) receiving element 26 designed to come into form-fitting engagement with at least one female (or male) receiving element 28 of the tool guiding device 8 and that the actuating/pressure element 16 of the decoupling device 12 has an operatively connected hook/bracket element 30 designed to comprise an undercut on the tool guiding device 8, preferably at least one pin element 44 extending from the tool guiding device 8 in transverse direction 32 to the longitudinal axis 34, so that in the closed state a disengagement of the receiving elements 26, 28 from each other is prevented. In a preferred manner, the male receiving elements 28 are cone-shaped.

Further, it may be provided that the base body 24 of the decoupling device 12 comprises a bearing journal which, viewed in transverse direction, is arranged preferably between the at least one male receiving element 26 and a seating recess 40 for a slide rod 11 of the telescopic device 10, and that the hook/bracket element 30 is pivotally arranged/mounted on the bearing journal, preferably at an angle of up to 30°.

Further, it may be provided that the pin element 44 of the tool guiding device 8 is of drop-shaped design when viewed in transverse direction and that, when the male receiving element 26 of the tool guiding device 8 is mated with the female receiving element 28 of the base body 24, the hook element 30 slides along the drop shape 44 and is thereby lifted so that the hook element 30 gets latched with the drop-shaped pin element 44 when the receiving elements 26, 28 are mated.

Further, it may be provided that the base body 24 of the decoupling device additionally comprises a stop pin extending in its transverse direction 32, which is preferably arranged between the bearing pin and a stop surface for the tool guiding device 8, and that a stop notch is additionally formed in the hook element 30, which is provided to form the pivot end stop of the hook element 30 by cooperating with the stop pin when the tool guiding device 8 is not latched in place.

An embodiment of the alignment device 1 for a tibial resection guide is provided in that its distal region 54 has a clamping device 2 comprising at least two clamping elements 4, 4*a* acting against one another for clamping the distal end of a tibia of a patient; the clamping elements 4 of the clamping device 2 being each of arcuate design and aligned with respect to each other so as to form an oval-shaped region 22 between them (in a closed state), as viewed in the direction of the longitudinal axis 20 of the alignment device 1, said oval-shaped region being designed for receiving the distal region of the tibia in a clamping manner, the clamping elements 4, 4*a* being each of resilient design so that the clamping device 2 of the alignment device (1) can be removed from the tibia (5) with one hand.

Further, it may be provided that the clamping elements 4, 4*a* are additionally designed so as to be fork-shaped and that the prongs 62 of the respective fork 60 are arranged in offset manner relative to one another such that in the closed state they engage into one another in an overlapping manner so that the tibia 3 is held in place.

Further, it may be provided that the respective tips 66 of the prongs 62 are shaped in opposite direction with regard to the respective arcuate shape of the clamping elements 4,4*a* so that the removal process from the tibia 3 is atraumatic.

Further, it may be provided that the (distal/close-to-hinge) ends 68 of the clamping elements/clamping forks 4, 4*a* are each enclosed/embraced and retained by a reinforcing element 70, which connects the respective clamping element 4, 4*a* to a respective latching element 74 bonded to a V-shaped contact block 86, the reinforcing element 70 being preferably made of plastics.

It may further be provided that the latching elements 74 each comprise a ratchet mechanism 76 so that the clamping elements/clamping forks 4, 4*a* can be pretensioned such that an adjustable pretensioning force acts on the tibia in the closed state 64.

Further, it may be provided that the V-shaped contact block 86, viewed in the longitudinal direction 20 of the alignment device 1, has a central contact area 78, from which lateral contact arms 82 each extend in a V-shape on both sides, with an angle C preferably in a region between 30° and 60°, more preferably in a region between 40° and 50° and in particular with an angle of 45°.

Further, it may be provided that the V-shaped bearing block 86 is coupled to a T-piece 92 via a spindle mechanism 90 in a laterally adjustable manner (resulting in an overall Y-shape in interaction with the bearing arms 82 of the bearing block 86), which is preferably adjustably connected to the telescopic device 10 of the alignment device 1 via a latching structure 94.

An embodiment of the alignment device 1 for a tibial resection guide comprises a (distal) clamping device 2 for clamping the distal end of a tibia of a patient;

a (proximal) tool guiding device 8 for guiding a tool during the resection of the tibia, a telescopic device 10 which is proximally connected/connectable to the tool guiding device 8 and distally connected/connectable to the clamping device 2 and designed to align the proximal and distal devices 2, 6 with respect to the tibia, the telescopic device 10 having a handle element 14 designed to receive, in extendable manner, a slide rod element 11 slidably mounted therein, wherein the telescopic device 10 comprises an arresting/securing element 104, which is arranged between the handle element 14 and the slide rod element 11 and which can be adjusted to reach a first position in which a first compressive force is effected between the elements 14, 11, which allows a braked relative displacement of both elements 14, 11, and which can additionally be adjusted to reach a second position in which a second compressive force is effected between the elements 14, 11, which arrests both elements 14, 11 relative to each other.

Further, it may be provided that the securing element 104 is additionally adjustable such that in a third position a third compressive force acts between the elements 14, 11 which allows a substantially unbraked relative displacement of both elements 14, 11.

It may further be provided that a locking element 112 is arranged between the securing element 104 and the telescopic device 10, which is designed to hold the securing element 104 on the telescopic device 10 in a locking position and to cause a release of the securing element 104 in a release position, so that the latter is removable from the telescopic device 10.

Further, it may be provided that the slide rod element 11 has a groove-shaped recess 118 in its longitudinal extension, which is provided to receive a clamping pin 120 of the securing element 104 and to guide it. The groove-shaped recess 118 advantageously provides a defined guidance of the clamping pin 120.

Further, it may be provided that the securing element 104 comprises an adjusting element 122 which acts on a spring element 124 of the securing element 104 in such a way that the pressure/clamping forces generated by the spring element 124 are adjustable in the respective positions 106, 108, 110.

Further, it may be provided that, when viewed in the transverse direction 32 of the alignment device 1, a receiving element/receiving portion 100 is arranged/formed on the handle 14 on the far side of the tibia, which is designed to receive the locking element 112 preferably in a movable manner.

Further, it may be provided that the slide rod element 11 has stops 128, 130 for the securing element 104 in its groove-shaped recess 118 at its two axial end portions in order to prevent the slide rod element 11 from sliding out of the handle element 14.

An embodiment of the alignment device 1 for a tibial resection guide comprises

- a clamping device 2 for clamping the distal end of a tibia 3 of a patient;
- a tool guiding device 8 for guiding a tool during the resection of the tibia,
- a telescopic device 10 proximally connected to the tool guiding device 8 and distally connected to the clamping device 2 and designed to align the devices 2, 8 with respect to the tibia 3, wherein the tool guiding device 8 has a seating recess 150 which is designed to receive, in a releasable manner, a contact device 6 for sensing the resection height.

Further, it may be provided that the seating recess 150 is a bore extending from the proximal top side 151 of the tool guiding device 8 along the longitudinal axis 20 of the alignment device 1 and that the contact device 6 comprises an insertion element/insertion mandrel 156 having a latching mechanism 154, which insertion element/insertion mandrel can be (axially) latched (and rotatably) inserted in the seating recess 150.

It may further be provided that the latching mechanism 154 has a lever element/an actuating lever 158, which is preferably arranged in/on the insertion mandrel 156 and via which a detent nose 160 can be actuated, which in the inserted state of the insertion mandrel 156 engages behind the seating recess 150 in order to hold the contact device 6 axially therein.

It may further be provided that the contact device 6 comprises a height sensing assembly 152 having a contact tip 166 arranged at the proximal end of a contact arm 338, which contact tip may be adjustably arrested on the tool guiding device 8 in longitudinal direction 34 and in transverse direction 32 of the alignment device 1.

Further, it may be provided that a spiral element 168 is provided between the insertion mandrel 156 and the contact tip 166 for adjustment in longitudinal direction 20, which preferably slidably/freely penetrates the contact arm 338 and is designed to readably output the height distance of the contact tip 166 relative to a cutting plane 170 of the tool guiding device 8.

Further, it may be provided that the spiral element 168 has a spiral wheel 172 which is held relatively rotatably thereon and is in screw engagement with the spiral element 168, which is preferably provided with numerical values 174 on its circumferential side and via which the height distance can be adjusted.

An embodiment of the alignment device 1 for a tibial resection guide comprises:

- a (distal) clamping device 2 for clamping the distal end of a tibia 3 of a patient;
- a (proximal) tool guiding device 8 for guiding a tool during the resection of the tibia,
- a telescopic device 10 with a handle 14 and a slide rod 11 slidably guided in the handle 14, the telescopic device 10 being proximally connected to the tool guiding device 8 and distally connected to the clamping device 2 and designed to align the devices 2, 8 (longitudinally) with respect to the tibia 3, wherein
- the telescopic device 10 comprises, in its proximal end region 52, a drive device mount 204 for receiving a drive device 202, which is formed by the slide rod 11 of the telescopic device 10 designed at least in sections as a hollow body. Preferably, the slide rod 11 completely penetrates the handle 14 in the longitudinal direction of the telescopic device 10 (in the design position) and thus forms the drive device mount 204 proximally to the handle 14.

Further, it may be provided that the drive device 202 can be inserted at its distal end into the hollow body portion of the slide rod 11 in such a way that a clamping of the drive device 202 in the hollow body section can be effected via a clamping mechanism 208 on the side of the drive device 202.

Further, it may be provided that the clamping mechanism 208 comprises an elongated control element 210 preferably in the form of a tension/compression rod, which is movably guided within a hollow body/support tube 408 of the drive device 202 and which is movable at its proximal region via a lever element 214 in longitudinal direction 20 in such a way that a (manual) actuating force acting on the lever element 214 can be effected on a clamping/cant element 216 clampable with the hollow body portion of the slide rod 11.

Further, it may be provided that the hollow body 408 of the drive device 202 has a chamfer 218 in its distal end/end face and that the cant element 216 also has a corresponding chamfer 220 at its end/end face facing the control element 210, so that the cant element 216 slides off on the hollow body 408 of the drive device 202 in the transverse/radial direction 32 when a tensile force is applied by the control element 210, so that the cant element 216 of the drive device 202 can be clamped to the slide rod 11 of the telescopic device 10.

Further, it may be provided that the drive device 202 in the inserted state is circumferentially flush with the slide rod 11 of the telescopic device 10 such that the tool guiding device 8 is movable in the longitudinal direction 20 along the slide rod 11 of the telescopic device 10 and along the hollow body 408 of the drive device 202.

Further, it may be provided that the drive device 202 comprises at its proximal end portion a transverse beam 222 which is longitudinally slidably mounted on the hollow body 408 of the drive device 202 substantially perpendicular to the hollow body 408 and which comprises at its free (proximal) end portion a fixation device 224 for proximal fixation of the alignment device 1 to the tibia 3. In an advantageous manner, the drive device 202 is supported to be freely movable in all three spatial directions (i.e. in the height direction along the hollow body 408, in the transverse direction along the transverse beam 222 and, if necessary, rotationally around the hollow body 408) by this embodiment and can thus be adapted to the respective boundary conditions.

A preferred embodiment of the alignment device 1 comprises:

- a (distal) clamping device 2 comprising at least two mutually pivotable clamping elements/clamping arms 4, 4*a* for clamping the distal end of a tibia 3 of a patient, which are mounted on a cantilever arm 93 designed to be inserted into a (distal) foot clamp reception device 5 on a telescopic device 10 of the alignment device 1,
- a tool guiding device 8 for guiding a tool during the resection of the tibia,
- the telescopic device 10, which is connected to the tool guiding device 8 and to the clamping device 2 and which is designed to align the devices 2, 6 with respect to the tibia 3, the telescopic device 10 comprising a handle element 14 which supports a slide rod element 11 so as to be longitudinally movable therein, wherein the alignment device 1 comprises a set 250 of slide rod elements, having at least a first slide rod element 254 with a first, short slide rod length and at least a second slide rod element 258 with a second, long slide rod length, the respective slide rod elements 254, 258 of the slide rod set 250 according to the invention being provided to be inserted into the handle element 14 as required, the respective slide rods 254, 258 of the slide rod set 250 in other respects being designed to be structurally identical to one another and in particular at their distal end portions being connected to/formed with a foot clamp reception device 5, and in that the ratio of the first length of the first slide rod element 254 to the second length of the second slide rod element 258 is preferably between 1 and 1.5, more preferably between 1.1 and 1.3 and in particular amounts to 1.27, so that different lengths of the tibia can be resected by the first and the second slide rod 254, 258 of the slide rod set 250, the length being measured from the proximal end of the slide rod 254, 258 up to the central axis 262 of the foot clamp reception device 5.

An embodiment of the alignment device 1 according to the invention provides that the clamping elements/clamping arms 4, 4*a* of the foot clamp reception device 5 are arranged to be axially offset with respect to the longitudinal direction of the cantilever arm 93, the cantilever arm 93 being insertable into the foot clamp reception device 5 by a respective rotation of 180° degrees in a first position and in a second position, so that in the first position the clamping elements 4, 4*a* are positioned toward the distal end of the alignment device 1 and in the second position toward the proximal end of the alignment device 1, as a result of which a height/length offset of the clamping elements 4, 4*a* in the longitudinal direction 20 of the telescopic device 10 is effected if the cantilever arm 93 is inserted into the foot clamp reception device 5 rotated by 180° degrees from the first to the second position.

Further, it may be provided that the height offset of the foot clamp reception device 5 is measured from the central axis 262 of the foot clamp reception device 5 to the respective articulation point 270 of the clamping elements 4, 4*a* and is preferably between 10 mm and 20 mm and in particular is equal to 15 mm.

The invention claimed is:

1. An alignment device, comprising: a telescopic device configured to be equipped with a saw block at a proximal end portion of the telescopic device; and an ankle shackle device that forms a clamping device at a distal end portion of the telescopic device, the clamping device comprising at least two clamping elements that are pivotable and configured to act against one another, for clamping a distal end of a tibia of a patient, the clamping elements each being of arcuate design, and each of the clamping elements being resilient at least in sections, such that the clamping device is removable from the tibia of the patient exclusively by utilizing a spring elasticity of the clamping elements, wherein the clamping elements are each fork-shaped with prongs arranged in an offset manner relative to one another such that in the closed state the prongs mesh with one another in an overlapping manner.

2. The alignment device according to claim 1, wherein the clamping device comprises a tibia contact block having two contact arms that are substantially V-shaped, rigid and diverging, the clamping elements being pivotally articulated to free end regions of the contact arms.

3. The alignment device according to claim 2, further comprising a ratchet mechanism via which the clamping elements are supported on the tibia contact block and by which the clamping elements are configured to be pretensioned independently of each other.

* * * * *